US011254633B2

(12) United States Patent
Navickas

(10) Patent No.: US 11,254,633 B2
(45) Date of Patent: Feb. 22, 2022

(54) CANNABIS THIN LAYER DECARBOXYLATION

(71) Applicant: Jonas Alcirdas Navickas, Hau'ula, HI (US)

(72) Inventor: Jonas Alcirdas Navickas, Hau'ula, HI (US)

( * ) Notice: Subject to any disclaimer, the term of this patent is extended or adjusted under 35 U.S.C. 154(b) by 66 days.

(21) Appl. No.: 16/602,455

(22) Filed: Oct. 7, 2019

(65) Prior Publication Data

US 2020/0299216 A1    Sep. 24, 2020

Related U.S. Application Data

(60) Provisional application No. 62/766,175, filed on Oct. 5, 2018.

(51) Int. Cl.
| | | |
|---|---|---|
| C07C 39/205 | (2006.01) | |
| C07C 37/56 | (2006.01) | |
| C07D 311/80 | (2006.01) | |
| A61K 31/05 | (2006.01) | |

(52) U.S. Cl.
CPC ............ *C07C 37/56* (2013.01); *C07D 311/80* (2013.01); *A61K 31/05* (2013.01); *C07C 39/205* (2013.01)

(58) Field of Classification Search
CPC ...... A61K 31/05; C07C 39/205; C07C 37/56; C07D 311/80
See application file for complete search history.

(56) References Cited

U.S. PATENT DOCUMENTS

| | | | |
|---|---|---|---|
| 4,279,824 A | 7/1981 | McKinney | |
| 7,344,736 B2 | 3/2008 | Whittle | |
| 7,968,594 B2 | 6/2011 | Guy | |
| 9,095,554 B2 | 8/2015 | Lewis | |
| 9,730,911 B2 | 9/2017 | Verzura | |
| 10,206,888 B2 | 2/2019 | Vu | |
| 2016/0219892 A1 | 8/2016 | Romanek | |
| 2017/0290869 A1 | 10/2017 | Whittle | |

FOREIGN PATENT DOCUMENTS

| | | | |
|---|---|---|---|
| CA | 2440070 A1 | 9/2002 | |
| CA | 2568997 C | 12/2005 | |
| CA | 2626074 A1 | 5/2007 | |
| CA | 2664315 C | 3/2008 | |
| CA | 2872528 A1 | 11/2013 | |
| CA | 2872689 A1 | 11/2013 | |
| CA | 2929321 A1 | 5/2015 | |
| CA | 2931486 A1 | 5/2015 | |
| WO | WO2016/205923 A1 | 12/2016 | |

OTHER PUBLICATIONS

Bai et al., caplus an 2018:2338376; 2018.*
Yao et al., caplus an 2019:1616478; 2019.*
Zhang et al., caplus an 2019:1726008; 2019.*
Eichler, M., Spinedi, L., Unfer-Grauwofer, S., Bodmer, M., Surber, C., Luedi, M., & Drewe, J. (2012). Heat exposure of Cannabis sativa extracts affects the pharmacokinetic and metabolic profile in healthy male subjects. Planta medica, 78(07), 686-691.
Taschwer, M., & Schmid, M. G. (2015). Determination of the relative percentage distribution of THCA and delta 9-THC in herbal cannabis seized in Australia—Impact of different storage temperatures on stability. Forensic Science International. 254,167-171.
Veress, T., Sznanto, J. I., & Leisztner, L. (1990). Determination of cannabinoid acids by high performance liquid chromatography of their neutral derivatives formed by thermal decarboxylation: I. Study of the decarboxylation process in open reactors. Journal of chromatography A, 520, 339-347.
Izzo, Angelo A., Borrelli, Francesca, Capasso, Raffaele, Di Marzo, Vincenzo & Mechoulam, Raphael. (2008) Non-psychotropic plant cannabinoids: new therapeutic opportunities from an ancient herb. Trends in Pharmacological Science. Article in press.
Russo, Ethan B. (2011). Taming THC: potential cannabis synergy and phytocannabinoid-terpenoid entourage effects. British Journal of Pharmacology. (2011)163,1344-1364.
Christelle, M. Andre, Hausman, Jean-Francois, & Guerriero, Gea. (2016) *Cannabis sativa*: The Plant of the Thousand and One Molecules. Frontiers in Plant Science. p. 1-17.
Hazekamp, A. et al.,(2007) Cannabis tea revisited: A systemic evaluation of the cannabinoid composition of cannabis tea. Journal of Ethnopharmacology. In press.
Wang, M., Wang, Y., Avula, B., Radwan, M. M., Wanas, A. S., Van Antwerp, J., Parcher, J. F., ElSohly, M. A., Kahn, 1. A., (2016) Decarboxylation Study of Acidic Cannabinoids: A Novel Approach Using Ultra-High-Performance Supercritical Fluid Chromatography/Photodiode Array-Mass Spectrometry. Cannabis and Cannabinoid Research, vol. 1.1, p. 262-271.
Pertwee RG (2008) The diverse CB1 and CCB2 receptor pharmacology of three plant cannabinoids: delta-9 tetrahydrocannabinol, cannabidiol, and delta-9 tetrahydrocannabivarin, British Journal of Pharmacology 153, 199-215.
Huestis, M. Human cannabinoid pharmacokinetics, Chemical Biodiversity Aug. 2007: 4(8): 1770-1804.
Iffland, K., Carus M., Grotenhermer F., Decarboxylatin of tetrahyrocannabinolic acid (THCA) to active THC. European Industrial Hemp Association paper. www.eiha.com.

(Continued)

*Primary Examiner* — Sun Jae Yoo
(74) *Attorney, Agent, or Firm* — Foley & Lardner LLP

(57) ABSTRACT

Dried and or decarboxylated *cannabis* containing a known composition of cannabinoids is blended with other dried or decarboxylated *cannabis* of a known composition of cannabinoids and or mixed with other extracts of, isolates of, cannabisor synthetic cannabinoids to achieve a prescribed amount of cannabinoids in the blend. Decarboxylated *cannabis* is preferentially produced using controlled thin layer decarboxylation. Precision decarboxylation is optionally used to produce a precise pair ratio of acidic to neutral cannabinoid, eg THCA to THC or CBDA to CBD. Further a prescribed or selected terpene profile is mixed and applied to the blend. Once mixed the plant material is suitable for ingestion without further treatment and is dosed appropriately.

13 Claims, 17 Drawing Sheets

(56) References Cited

OTHER PUBLICATIONS

Pertwee R., 2015, New potential therapeutic applications for certain phytocannabinoids revealed by pharmacological discoveries. University of Aberdeen. https://cannabis-med.org/members/wp-content/uploads/2015/11/Pertwee.pdf.

Russo E., 2017 Cannabis Pharmacology: The usual suspects and a few promising leads. Download at ethanrusso@comcast.net or www.phytecs.com.

* cited by examiner

Fig. 2

Legend for Fig. 1- Pharmacologic actions of major non psychotropic cannabinoids

D9 THC    Delta9-tetrahydrocannabinol
D8 THC    Delta8-tetrahydrocannabinol
CBN    Cannabinol
CBD    Cannabidiol
THCV   tetrahydrocannabivarin
CBC    cannabichromene
CBG    cannabigerol
THCA   tetrahydrocannabinolic acid
CBDA   cannabidiolic acid
TRPV1  transient receptor potential vanilloid type 1
PPAR   peroxisome proliferator-activated receptor
ROS    reactive oxygen species
5HT-1A    5-hydroxytryptamine
FAAH   fatty acid amide hydrolase
CB1    cannabinoid receptor type 1
CB2    cannabinoid receptor type 2
GABA   gammaaminobutyric acid
TNF    tumor necrosis factor
Ca     calcium
Id-1   DNA binding protein inhibitor ID1

FIG 4    LEGEND for Synthetic/Decarboxylation/Metabolic Cannabinoid Map Fig 3

OVA    olivetoic acid
GPP    geranyl diphoshphate
CBGAS    cannabigerolic acid synthetase
DVA    divarinic acid
CBGA    cannabigerolic acid
CBGVA    cannabigerovarinic acid
THCAS    tetrahydrocannabolic acid synthetase
CBDAS    cannabidiolic acid synthetase
CBCAS    cannabichomenic acid sythetase
CBNA    cannabinolic acid
THCA    delta 9 tetrahydrocannabinolic acid
CBDA    cannabidiolic acid
CBCA    cannabichomenic acid
CBLA    cannabicyclolic acid
THCVA    tatrahyrocannabivarinic acid
CBDVA    cannabidivarinic acid
CBCVA    cannabichrovarinic acid
CBN    cannabinol
THC    delta 9 tetrahydrocannabinol
CBD    cannabidiol
CBC    cannabichromene
CBG    cannabigerol
CBGV    cannabidogerovarin
THCV    tetrahydrocannabivarin
CBCV    cannabidivarin
8THC    delta 8 tetrahydrocannabinol
CBL    cannabicyclol
CYP450    cytochrome P450
CYP4502C9    cytochrome P450 subtype 2C9
CYP4503A4    cytochrome P450 subtype 3A4
11-OH-THC    11-hydroxy-tetrahydrocannabinol
THC-COOH    3,11-Nor-delta9-tetrahydrocannabinol-carboxylic acid
7-OH-CBD    7-hydroxy-cannabidiol
7-COOH-CBD

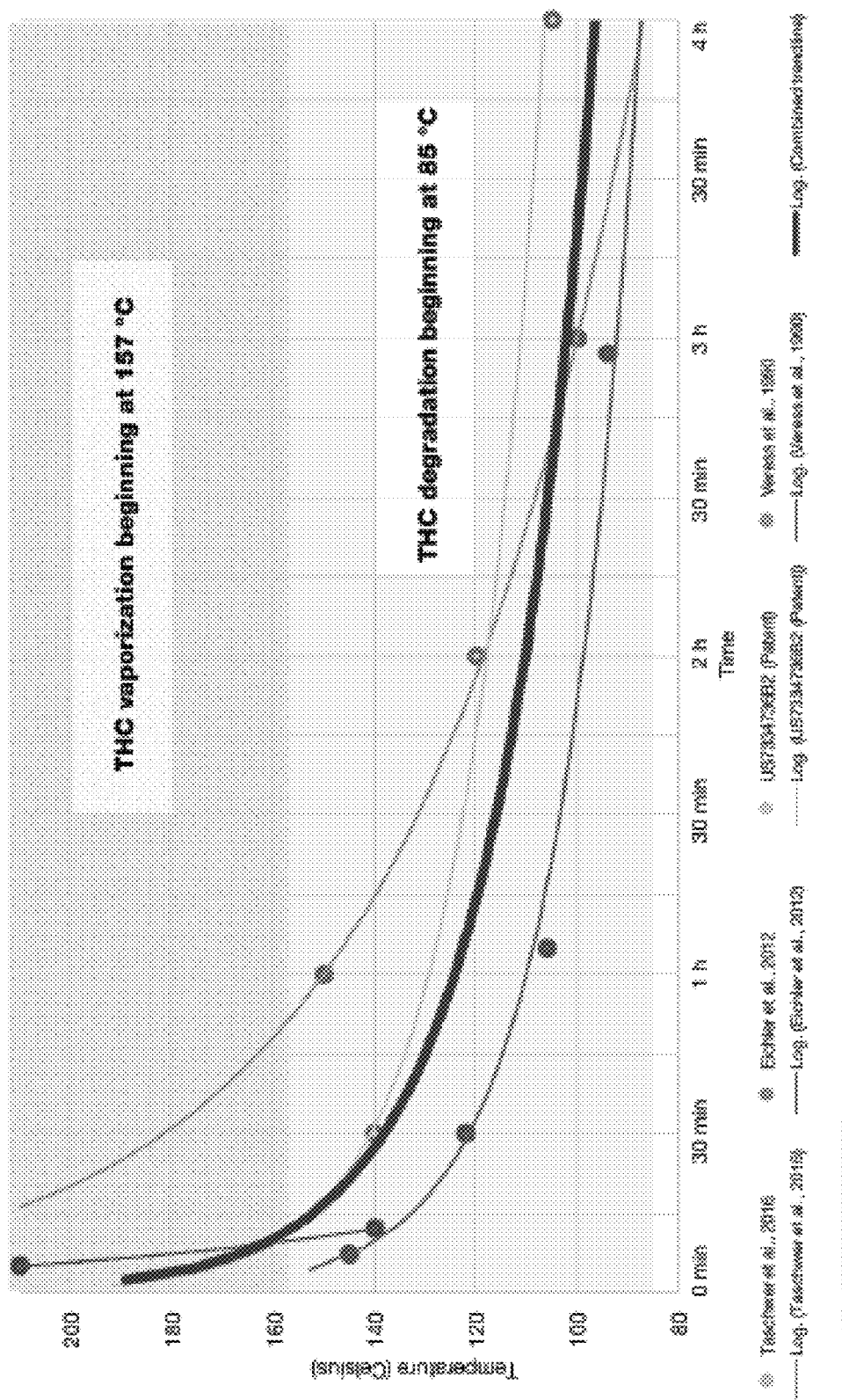
FIG. 5 Complete THCA decarboxylation to THC

Experimental results for THCA-A, Δ9-THC and CBN at 110°C.

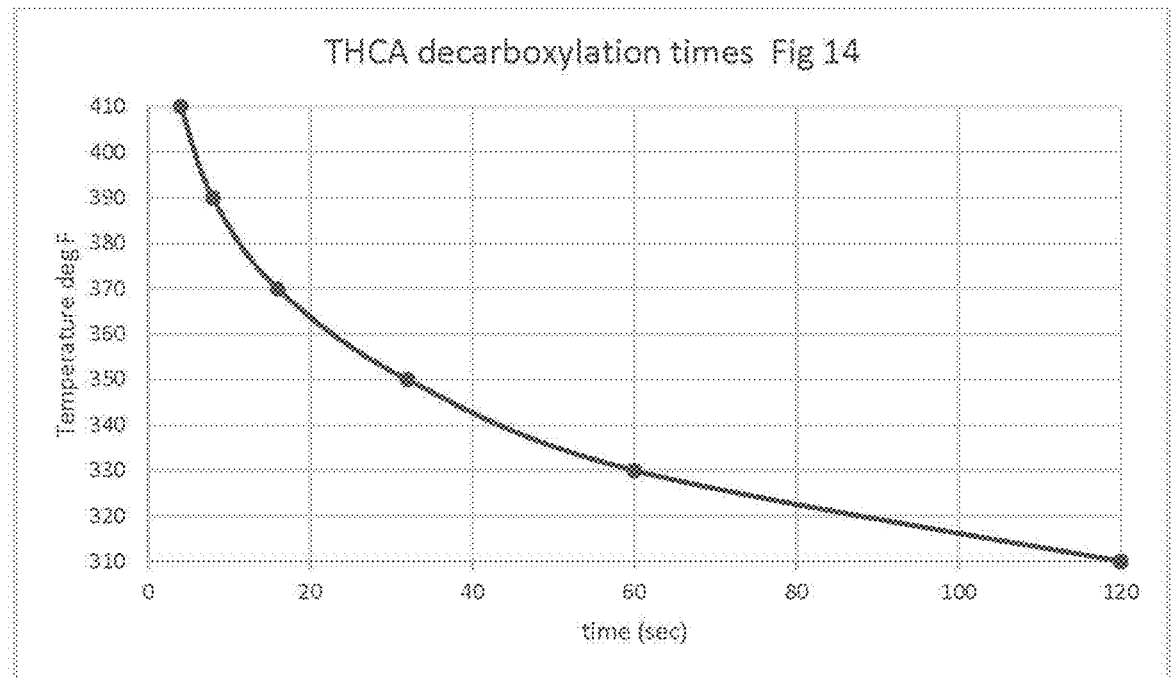
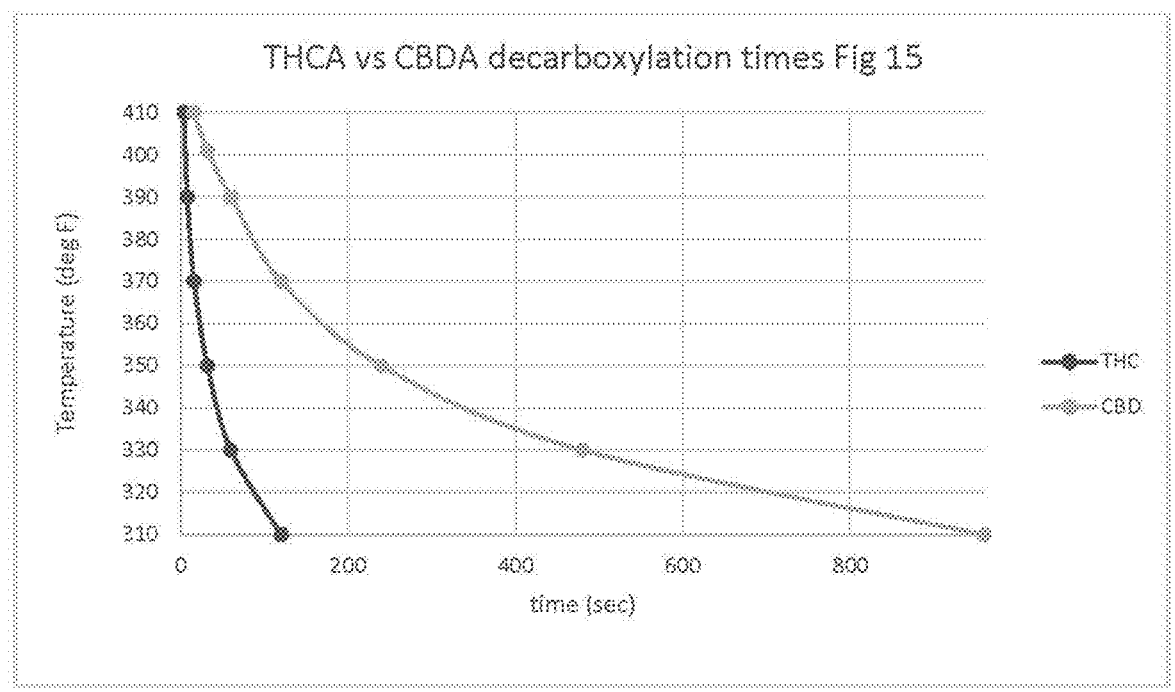

Fig 18 a
10  10
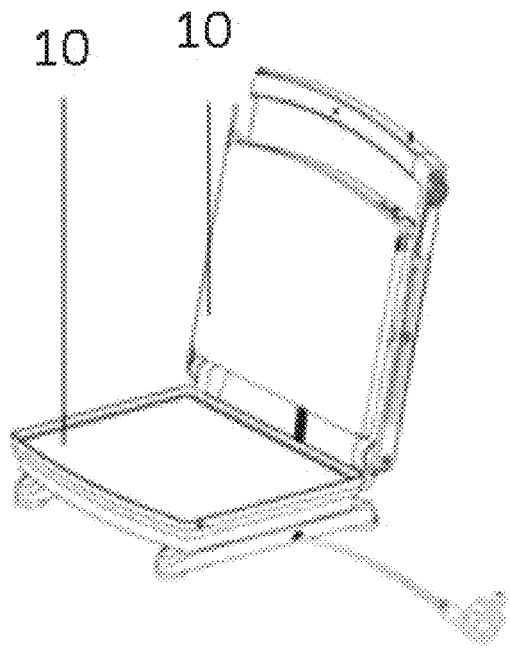
Fig 18 b
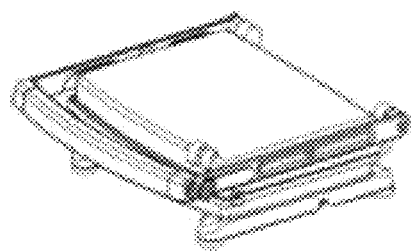
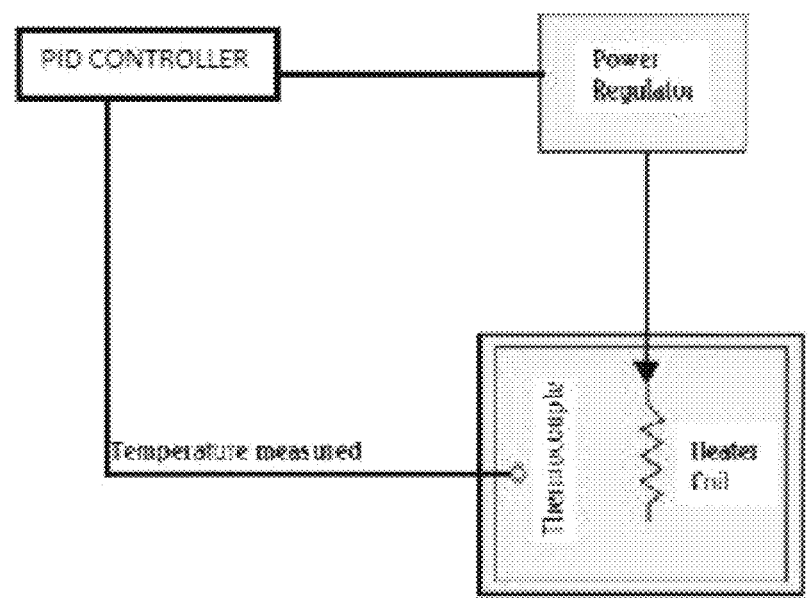
Fig 19

CANNABIS THIN LAYER DECARBOXYLATION

CROSS REFERENCE TO RELATED APPLICATIONS

This application claims benefit of provisional patent application U.S. 62/766,175 filed Oct. 5, 2018 by the present inventor.

NON PATENT LITERATURE DOCUMENTS

Eichler, M., Spinedi, L., Unfer-Grauwofer, S., Bodmer, M., Surber, C., Luedi, M., & Drewe, J. (2012). Heat exposure of *Cannabis sativa* extracts affects the pharmacokinetic and metabolic profile in healthy male subjects. Planta medica, 78(07), 686-691.

Taschwer, M., & Schmid, M. G. (2015). Determination of the relative percentage distribution of THCA and delta 9-THC in herbal *cannabis* seized in Australia-Impact of different storage temperatures on stability. Forensic Science International. 254, 167-171.

Veress, T., Sznanto, J. I., & Leisztner, L. (1990). Determination of cannabinoid acids by high performance liquid chromatography of their neutral derivatives formed by thermal decarboxylation: I. Study of the decarboxylation process in open reactors. Journal of chromatography A, 520, 339-347.

Izzo, Angelo A., Borrelli, Francesca, Capasso, Raffaele, Di Marzo, Vincenzo & Mechoulam, Raphael. (2008) Non-psychotropic plant cannabinoids: new therapeutic opportunities from an ancient herb. Trends in Pharmacological Science. Article in press.

Russo, Ethan B. (2011). Taming THC: potential *cannabis* synergy and phytocannabinoid-terpenoid entourage effects. British Journal of Pharmacology. (2011)163, 1344-1364.

Christelle, M. Andre, Hausman, Jean-Francois, & Guerriero, Gea. (2016) *Cannabis sativa*: The Plant of the Thousand and One Molecules. Frontiers in Plant Science. P. 1-17.

Hazekamp, A. et al., (2007) *Cannabis* tea revisited: A systemic evaluation of the cannabinoid composition of *cannabis* tea. Journal of Ethnopharmacology. In press.

Wang. M., Wang, Y., Avula, B., Radwan, M. M, Wanas, A. S., Van Antwerp. J., Parcher, J. F., ElSohly, M. A., Kahn, I. A., (2016) Decarboxylation Study of Acidic Cannabinoids: A Novel Approach Using Ultra-High-Performance Supercritical Fluid Chromatography/Photodiode Array-Mass Spectrometry. Cannabis and Cannabinoid Research, Vol. 1.1, p 262-271.

Pertwee R., 2015, New potential therapeutic applications for certain phytocannabinoids revealed by pharmacological discoveries. University of Aberdeen. https://cannabis-med.org/members/wp-content/uploads/2015/11/Pertwee.pdf Russo E., 2017 *Cannabis* Pharmacology: The usual suspects and a few promising leads. Download at ethanrusso@comcast.net or www.phytecs.com

U.S. PATENT DOCUMENTS

| | | | |
|---|---|---|---|
| 9,730,911 | B2 | /2017 | Veruza et al |
| 7,968,594 | B2 | /2011 | Guy et al |
| 10,206,888 | B2 | /2019 | Vu et al. |
| 7,344,736 | B2 | /2008 | Whittle et al |
| 0290869 | A1 | /2017 | Whittle et al |
| 9,095,554 | B2 | /2015 | Lewis et al. |
| 968,594 | B2 | /2011 | Guy et al. |
| 0219,892 | A1 | /2016 | Romanek. |
| 4,279,824 | | /1981 | McKinney. |

BACKGROUND OF INVENTION

When one sees the available pharmacological uses of cannabinoids and terpenes it is frustrating to not have them easily available. Currently most commonly used are blended oils mixed with terpenes. Some are useful for oral ingestion, most are designed for smoking or vaping.

It seems daily we learn more about cannabinoid and terpene pharmacologic activities, synergies, their breeding, extraction, in particular as they relate to non-psychoactive, medical or therapeutic use, FIG. 1. FIG. 3 illustrates the synthesis, decarboxylation and metabolism of phytocannabinoids. Most notable are the principal acidic and neutral couples that are manipulated with decarboxylation, namely THCA/THC, CBDA/CBD, CBCA/CBC, CBGA/CBG, THCVA/THCV, CBDVA/CBDV, CBCVA/CBCV and CBGVA/CBG.

Particularly not made available today are the acidic forms of the cannabinoids in currently available cultivars. For example CBDA and THCA. These are demonstrating to be particularly active in various cancers, affecting cell proliferation and apoptosis. Their combination with CBD in particular may be an effective modality for decreasing cell proliferation, signs of oxidative stress and enhancing neuroprotection.

Multiple patents and current practice usually address the THC to CBD ratio. The CBD seems to mitigate the adverse effects of THC at the doses used. With successful breeding, cultivars high in CBG and CBC are becoming available. Cultivars high in the individual isolated propyl cannabinoids should be forthcoming. We can then expect the relevant ratios to come to include all the available pentyl and propyl cannabinoids. At that point it is possible to completely customize the available cannabinoid content.

In the meantime terpene content can be customized completely by formulating exogenous terpenes.

Now there is a dependence on existing cultivars, extraction and blending until leaders succeed in breeding cultivars for conditions or activity.

Studies have demonstrated patient preference for smoking the whole plant more than ingesting plant extract or synthetic THC. The whole plant may be preferable in oral preparations. The whole plant would have presumable beneficial effects from the plant matrix components. Synergistic components can remain available which might otherwise be separated out in an extraction. The benefits might simply be nutritional from compounds such as fatty acids, sterols and even fiber.

Making the whole plant available can eliminate some problems inherent in extraction procedures. For example current processes generate CBN as a byproduct. This is extracted along with the desired cannabinoids and remains in the product.

This production of CBN as a byproduct is caused by degradation of THC in the step prior to extraction, during the process of decarboxylation. The current processes of decarboxylation produce the degradation as noted and are highly variable in their predictions of complete decarboxylation.

The main use of decarboxylation to present is to achieve complete decarboxylation of an acidic form to a neutral form of a cannabinoids for example from THCA to THC. THC has been the desirable cannabinoid, renowned for its intoxicating effects. After decarboxylation the THC is typically extracted as an oil. The plant material is decarboxylated first as the THCA is not convenient to extract then decarboxylate.

Multiple factors are involved in the decarboxylation. Mostly, they have not been considered previously.

The pharmacological actions of non-psychotropic cannabinoids as seen in are wide-ranging with many of the cannabinoids demonstrating useful activities. CBD is the most widely represented and studied. It has anxiolytic, antipsychotic, antiepileptic, neuroprotective, vasorelaxant, antispasmodic, anti-ischemic, antiproliferative, anticancer, antiemetic, antibacterial, antidiabetic, anti-psoriatic, intestinal anti-Pro kinetic, analgesic, bone stimulating, anti-inflammatory and immunosuppressive activity. FIG. 1.

Much has been learned of the endocannabinoid system in recent decades. Most of the activity of CBD has been attributed to its stimulating interaction with the CB2 receptor and it's inhibiting effects of THC at the CB1 receptor. The diagram demonstrates that of all the CBD activity indicated only one is actually mediated by the CB two receptor, namely the antiproliferative and anticancer activity, FIG. 1.

It may be useful to combine cannabinoids with similar activities for synergistic effect. For example anticancer and antiproliferative activity is demonstrated by CBD, CBG, CBC, CBDA and THCA. CBG and CBC cultivars are only recently becoming available and not yet widespread. CBD, CBDA and THCA are presently available from widely available cultivars. CBDA and THCA extracts are occasional available at *cannabis* dispensaries.

It is common to see CBD and THC combined for use in a variety of pathologies. The combination usually is a prescribed or indicated ratio of CBD to THC the titrated to dose. With the availability of more and more cannabinoids a more useful ratio prescription might indicate the ratio for the acidic and neutral cannabinoids of a particular cannabinoid pair for example CBDA is the precursor to CBD. THCA is the precursor to THC.

The conversion of THCA to THC and CBD a to CBD or any acidic cannabinoid occurs via decarboxylation. This involves release of a carboxylic acid group from the acidic form transforming the molecule to its neutral form.

PRIOR ART

FIG. 5 is a commonly referenced graph to predict decarboxylation times and temperatures. A common anecdotal method for DIY baking or oil extraction is to heat *cannabis* at 100° C. for 60 minutes to decarboxylate. Interpreting the data from the graph the fastest conversion at 100° C. is by Veress at 105 minutes almost twice the anecdotal recommendation. Next is Taschwer at 180 minutes and U.S. Pat. No. 7,334,736B2 at four hours. In other words the range is 105 to 240 minutes for 100° C.

Further examination of the curves show similar wide ranges for a given temperature for complete conversion. For example at 120° C. range is 30 minutes to two hours, at 140° C. it is 15 minutes to 75 minutes and at 150° C. is seven minutes to one hour.

Eichler references the decarboxylation temperature of 200° C. for five minutes for THC. The reference could not be corroborated. No details were given regarding the conversion methodology. These would be extreme conditions compared to the 150° C. at seven minutes for Verness. Eichler cites his actual experimental conditions as 140° C. for 12 minutes.

If the 200° C. point is ignored as an outlier is clear all the work reported here is at 150° C. or less.

These are very significant variances in prediction of peak conversion times. This can lead to incorrectly estimating the time to complete conversion, if too short, leading to incomplete conversion, and if too long excessive degradation. The author suggests the variances may be related to the methodologies used.

Taschwer and U.S. Pat. No. 7,334,736B2 used convection heating in ovens and had the longest times. Verness was most rapid, using conductive heating of an extract in a test tube placed in a heated block and open to the atmosphere. Eichler uses extract, no decarboxylation or methodology is described.

The prolonged times for heating with convection indicate an inefficient heat transfer. This is coupled with extended opportunity for degradation of product. U.S. Pat. No. 7,334,736B2 using 145° C. (293° F.) at 45 minutes. Using their table 2 and interpolating to 145° C. (293° F.), the stated temperature for their decarboxylation the CBN content is 12 to 15%. It is in their claims as less than 10%.

DIY

The long time required in convection ovens could be limiting in a production setting. Even for an individual it may be inconvenient. Many individuals prepare oils, butters and may decarboxylate for the extraction or for use in edibles. Previous DIY methods for decarboxylation recommended 100° C. (212° F.) for one hour. Now recommendation is 275° F. (135° C.) for 20 minutes (Edibles, Hua, 2018). This is compared to 145° C. (293° F.) for 40 minutes in U.S. Pat. No. 7,334,736B2 Whittle, which also includes a preheating for 15 minutes at 100° C. (212° F.) to drive off water.

The conditions in an oven at 275° F. (135° C.) are likely to approach or even exceed the deteriorating effects noted at 120° C. (240° F.) in, FIG. 6E. At 120° (204° F.) in an open reactor the loss of converted CBD was 45-55% compared to the closed reactor condition at the same temperature, FIG. 6E. This seems more related to open reactor conditions rather than the absolute temperature.

The open reactor conditions at 100° C. (212° F.), FIG. 6C, show a loss of about 28% THC relative to the conditions demonstrating the least loss of THC and highest conversion (120° C., closed reactor), FIG. 6F. The open reactor conditions at 110° C. (230° F.), FIG. 6*d*, similarly show a loss of about 28% compared to that maximally achieved at 120° C. in the closed reactor. The 120° C.). (230° closed reactor demonstrates an approximately 10% loss of total THC (THC A+ THC) from the starting condition.

Factors

Prior art does not discuss many applicable factors in the decarboxylation process, namely heating method, retained water, form of the *cannabis*, volume of plant material, volume of the reactor and open or closed reactor.

Heat

Convection

The gas in a convection oven under normal circumstances is air. In convection heating air absorbs heat from the heating source. It then moves throughout the oven on convection currents produced by heating and cooling air. When an air molecule contacts another molecule heat transfers from the hotter molecule to the cooler one. This is relatively infrequent as compared to a solid since air contains few molecules in contact.

Heating of a pile of dried plant material in an oven occurs mostly by convection. This will be assisted somewhat through conductive heating by the container. Since air movement throughout the pile is limited heating will occur mostly at the surface which is then conducted and radiated toward the interior of the pile, ultimately heating the entire pile.

A large free space in the oven will allow better temperature stability due to a larger volume of heated air. The reserve heat capacity will also increase minimizing temperature changes. A larger free space though will increase open reactor effects such as vaporization and degradation.

Radiant

A hot surface emanates infrared radiation proportional to its temperature and in all directions. It decreases with distance from the source according to Beers law. The energy will dissipate logarithmically with the distance from a given source. This means that at twice a given distance the intensity is one quarter of the original, or at half the distance the intensity is four times the original.

Conductive

In conductive heat transfer the infrared energy contained in one molecule is transferred directly through contact with another molecule. For example from a heating surface to a container to contained oil.

An example of the three types of heating, the intensity of which can be palpable, despite the same temperature follows. A cast-iron skillet is placed in a 350° F. oven until it reaches thermal equilibrium. If one were to place a hand in the 350° oven the heat would be apparent but the hand could be maintained there for probably several seconds. This is the convective heat. As the hand approached the surface of the pan a different type of more intense heat would be sensed the closer the hand came to the surface. Just before reaching the surface this kind of heating reaches its maximum. The tolerance to maintaining the position here would be much shorter than at a distance. This is the radiant heat. If the hand were to touch the surface the heat transfer would be immediate and extremely rapid compared to the radiant are convective heat. Even with minimal contact a burn is likely to result. This is the result of direct conductive heat transfer from the pan to the finger.

Water

Generally preheating is required to remove any remaining water from the "dried" *cannabis*".

Any presence of water remaining during heating will cause a plateau in the temperature of the heating plant matter. This will limit the temperature to that of the boiling water converting to steam until all the water is volatilized. Further heating will increase temperature of the plant matter to that of the plates. This outgassing occurs very rapidly. With the thin layer method at 300° F. it takes about 10-15 seconds for the water to boil off. At 400° F. the total decarboxylation takes 10 seconds, the outgassing of the water must be extremely rapid, on the order of one second or less.

the water is released as steam during the heating process. At that temperature, 212° F. (100° C.), the terpenes are volatilized and carried off with the steam, effectively a steam distillation. This removes the majority of terpenes from the *cannabis* plant material.

Volume

The volume of the substance being heated will affect the time required to distribute the heat throughout the volume. A larger volume will require more time.

With a large pile of *cannabis* material in a convection oven the "cake pan" effect becomes evident. In a convection oven heat must be transferred from the heated air to the surface of the cake. Some heat is also absorbed through contact with the pan. The plant is a poor conductor of heat. It will take time to bring the interior of the pile up to temperature, while the exterior continues to heat. As the moisture decreases throughout the pile, conductive heat movement slows. Continued exposure at the surface and continued heating for continued time predisposes the exterior to oxidation and degradation reactions. In the case of THC, CBN is the degradation product.

Thin Layer

As volume of plant increases in thickness the cake pan effect increases. As the thickness of the layer decreases to a thin layer the entire depth of the material approaches the "surface condition" of the cake as there remains very little interior. Therefore water release and decarboxylation are rapid as the entire volume reaches the same temperature rapidly.

The process is limited by the thickness of the plant matter. As the thickness increases along with the volume the mass of the plant matter approaches a cake pan configuration. As such the heating, water release and decarboxylation occur at different rates at the surface and interior of the cake. At the surface of the cake the heating will be fastest along with the water release and decarboxylation. In the interior of the cake it will require longer time to reach the oven temperature resulting in slower water release and slower decarboxylation.

The ideal thickness of the thin layer is mostly related to the thermal capacity of the heating plates. As the size of the plates increases the thermal mass increases and fluctuations in temperature will be minimized to the small mass of the *cannabis* relative to the thermal capacity of the heated plates. A rule of thumb to determine whether the thermal capacity is adequate for the thin layer, is that the retained water should steam off in about 10% of the total heating time to ensure the step function like heating of the thin layer.

Small volumes of *cannabis* are easily and rapidly decarboxylated in a thin layer method. Complete decarboxylation or precision decarboxylation is easily achieved. This makes it ideal for varying individual prescriptions. The amounts of individual components stocked in a formulating dispensary can be less because of the rapid and controllable available heating, meaning less stocking of individual cannabinoids. In other words the stock may be limited to the acidic forms and the neutral forms can quickly be generated without needing to stock them.

Current ovens can be used for thin layer methods. Two stacked heated plates are on a slidable rack. The entire interior of the oven is packed with these racks carrying two plates each. As a rack is slid out, it's plates can be separated through manual or mechanical means and the contained thin layer is removed or inserted as necessary.

Form

Plant

Dried plant material becomes a poor conductor of heat once its water content is removed. It will take longer to heat then an extract. Heat absorbed by an extract or oil is conductive at the heating surface then moves throughout the solution by convection. This is much faster than the convective heat of dried plant material in an oven.

FIG. 6D demonstrates peak CBD at 90 minutes at 110° C. for *cannabis* oil in an open vial in an oven. Comparatively Taschwer shows peak CBD for plant material in a 110° C. oven at 135 minutes, a 50% increase for the plant material over the time for the oil.

Volume of Extract

As volume of an extract increases it begins to have more resemblance to a solid. Conduction heating would be most effective. Convection heating to bring an oil to temperature, would be most inefficient.

Evaporated Extract

Veress 1990 uses a few drops of extract in the bottom of an open glass test tube placed in a borehole in a heated metal block. In comparing methods this is very different than U.S. Pat. No. 7,334,736B2, processing 6 kg (13.2 pounds) plant material in a convection oven.

Open Versus Dosed Reactor

Open reaction chambers lead to atmospheric exposure, allowing an oxidizing environment and degradation.

FIG. 6 shows the effects of increasing temperature and closing the reactor. The lines represent CBDA concentration, CBD concentration and their sum. At 80° C., FIG. 6A, and 90° C., FIG. 6B, the sum stays constant indicating no degradation. At 100° C., FIG. 6C, and 110° C. (230° F.), FIG. 6D, the sum decreases significantly indicating loss of both CB D and CBDA. At 120° C. (240° F.), FIG. 6E, shows rapid loss of CBDA with incomplete conversion to CBD.

This condition indicates the greatest loss at 120° C. and open reactor, FIG. 6E. With the closed reactor there is very little total loss, maximal total conversion and most rapid maximal conversion, 6F. Therefore the closed reactor compared to an open reactor at this temperature is more advantageous.

These advantages are maintained in the thin layer method at its temperatures typically at 300° F. (150° C.) or more.

A thin layer, closed reactor has less possible volatility and vaporization loss. Further it has less exposure to oxidation and degradation.

CBGA at 110° C. is remarkable in that the sum decreases by half in the time decarboxylation is maximized, FIG. 7. This is indicating a 50% loss of total CBG. The decay and tailing of the CBGA curve show typical shape and decay to zero, indicating complete consumption of CBGA. The CBG curve barely doubled from its initial value. This indicates that it is the CBG that is decreased from the expected values. This indicates either incomplete formation, side reaction, volatilization or degradation. The temperature should have been adequate for decarboxylation. Side reactions were not monitored. This methodology used an extract oil, in open vials heated in a vacuum oven. While the vacuum oven minimizes oxidative degradation, the vacuum itself at these conditions may accelerate vaporization of the CBG.

There is a lot of confusion in the literature about the terminology of *cannabis*. We need to be more specific in our discussions of medicinal cannabinoids. In the literature of the last several decades it is common to refer to any use of any cannabinoids as *cannabis*. Particularly extracts which are being researched, are in discussions called *cannabis*. When the only significant cannabinoid of interest was THC this was not unreasonable. Now however other THC related chemicals are becoming relevant, such as THCA, Delta 8 THC, CBNA, CBN, THCV A, THCV, and their metabolites. Similarly the precursors and metabolites of CBD, CBG, CBC, CBDV, CBGV, and CBCV are becoming more known, widespread and studied.

Further a myriad of synergistic terpenes makes for a true alphabet soup rather than "*cannabis*". Research reports may conclude that "*cannabis*" may or may not have effects on the studied condition. Again without specifying the form (plant, extract, isolate, synthetic) and the likely predominant cannabinoid and terpene spectrum, reference and conclusion to "*cannabis*" is incomplete and misleading. The term *cannabis* is best reserved to the whole plant. Specific cannabinoids of interest should be mentioned as such. The modality of ingestion, smoking, oral, sublingual etc. as well as form of *cannabis*, whole plant, decarboxylated, oil, tincture etc. are specific characteristics that are noteworthy and can affect outcomes.

"*Cannabis*" as used herein refers to the dried plant material, typically female flowers, though cannabinoids are contained in various parts of the plant.

Formulating

Formulating cannabinoids and terpenes for oral use has been done previously using oil based extract. For example U.S. Pat. No. 7,344,736 patent blends previously extracted oils to modify cannabinoid content of an oil based product. U.S. Pat. No. 10,206,888 Vu 2019 modifies cannabinoid and terpene content in whole plant material for a limited application. The intended use for the modified plant material is for smoking. No consideration is given for oral use. Further no consideration is given to use or availability of any acidic cannabinoids. No consideration is given for decarboxylation as part of the method.

BRIEF SUMMARY OF THE INVENTION

Objectives

To simplify and speed up production of *cannabis* containing a prescribed amount of cannabinoids and terpenes.

Eliminating need for extraction. No solvents or chemical treatment.

Making available acidic cannabinoid forms.

Eliminating need for smoking or vaporization. Ideal for oral ingestion.

Quick turnaround time for customization of *cannabis* for prescribed actions.

To provide any benefits of non-extracted fractions of the plant material matrix.

To optimize cannabinoids and terpene blend for desired actions.

Amenable to small scale, individual, rapid use.

Precision to allow partial, predictable decarboxylation.

Allows for smaller stock to be carried by dispensary, no need to stock both acidic and neutral forms Advantages of thin layer. Predictability, reproducibility, minimize waste through evaporation, oxidative degradation, or incomplete conversion, speed, and efficiency. Ability to make all cannabinoids and terpenes available, particularly the acidic moieties.

It Is desirable to have a cannabinoid formulation generated from whole plant material that is, safe, non-intoxicating. It is preferably administered orally. Though the product can be smoked it is not preferable. It should be customizable for multiple desired effects and activities. Further it is ideally rapid, and allow small quantities of material to be customized. It would integrate well in a dispensary setting to provide real-time custom, prescribable *cannabis*. In a dispensary setting it would be desirable to stock the acidic form of the plant. It could be rapidly converted to their neutral cannabinoid form rapidly for blending.

The process produces partially or completely decarboxylated *cannabis*.

Method of using decarboxylated *cannabis*. The decarboxylation is from the predominant acidic cannabinoid in the cultivar into the neutral cannabinoid in the acid/neutral pair. The amount of the decarboxylation is specified, partial or complete. This is indicated by specifying a ratio of the acidic to neutral components, for example 1:1 THCA:THC. The cannabinoids are chosen and combined to maximize desired pharmacologic activity through specific activity of the cannabinoids or their synergy.

Additional components of other acid/neutral pairs can be generated. For example a 1:1 ratio of CBDA:CBD. These are blended with the previous pairing.

When a thin layer of dried *cannabis* is heated with contact from both sides conductive heating is maximized from both sides. The radiant heat emitted from the plates is also greatest closest to the plates. As the two plates are opposed against the thin layer the short distance between the plates will create a high radiant field, reinforced from both sides by the proximity of the two surfaces. The summation of the two radiant fields combined with the conductive transfer produces a uniformly heated space in the thin layer cavity.

Precise control of the heating allows predictable times and conversion rates with good accuracy. This method essentially uses a step function in controlling the heat. Placement of the foil packet between the heated plates raises the temperature of the packet to that of the plates almost instantaneously except for any existing water content. At the temperatures utilized and with the thin layer the water vaporizes very quickly, proportional to the temperature, typically 15 seconds or less.

It is the precise control of temperature of the *cannabis* material being decarboxylated that is critical. The length of time they *cannabis* material is at a given temperature determines how long the conversion will take. It is difficult to have all the *cannabis* material reach a given temperature quickly and rapidly in a convection oven. Using the thin layer method with conductive and radiant heat the entire mass of the *cannabis* material reaches and stabilizes at the same temperature throughout rapidly. In convection heating this heat distribution issue can be mitigated somewhat by stirring the *cannabis* material throughout the decarboxylation process, however this exposes more of the material for degradation in the atmosphere.

Once a rapid precise repeatable, small-scale decarboxylation process is available it allows prescription level blending of cannabinoids and terpenes. This is useful for individuals or dispensaries. Decarboxylated whole plant provides a backdrop of the biological matrix and other potentially useful synergistic compounds that are typically discarded during processing to extracts. From the cannabinoid and terpene standpoint a completely decarboxylated plant is essentially void of terpenes and acidic cannabinoids.

This allows an opportunity to maintain benefits of the whole plant, while customizing the cannabinoid and terpene content for specific uses. This is particularly useful on small scales for individuals to allow access to prescriptive grade *cannabis* medicines. It further allows prescribers to formulate their own prescriptions based on knowledge of the cannabinoid actions and make adjustments as deemed necessary. It allows rapid turnaround time for these adjustments without waiting for a pharmaceutical company to shift production to new formulations, which economically would require large volumes, and be inordinately time-consuming for any individual patient.

BRIEF DESCRIPTION OF THE SEVERAL VIEWS OF THE DRAWINGS

FIG. 2 Legend for FIG. 1 Pharmacological actions of non-psychotropic cannabinoids FIG. 5 shows THCA decarboxylation summary curves

FIG. 14 shows THCA decarboxylation times using the thin layer method FIG. 15 shows THCA and CBDA decarboxylation times using the thin layer method

FIG. 18 shows FIG. 18*a*, the hinged plates reactor in the open position and 18*b* in the closed position FIG. 19 shows the schematic for the PID temperature controller and the hinged plates reactor

DRAWINGS—REFERENCE NUMBERS

Figure 1:
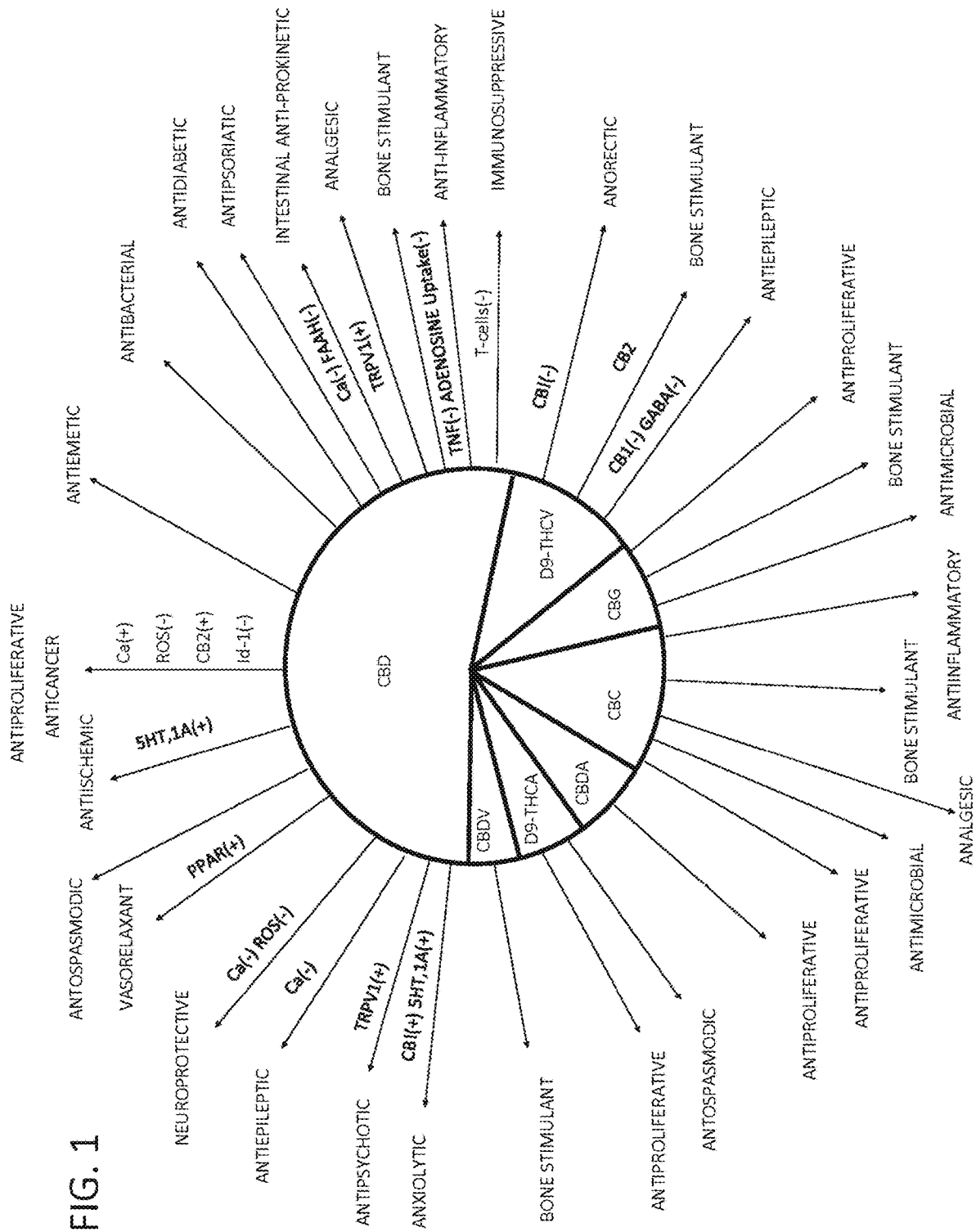
FIG. 1 shows Pharmacological actions of non-psychotropic cannabinoids
Figure 3:
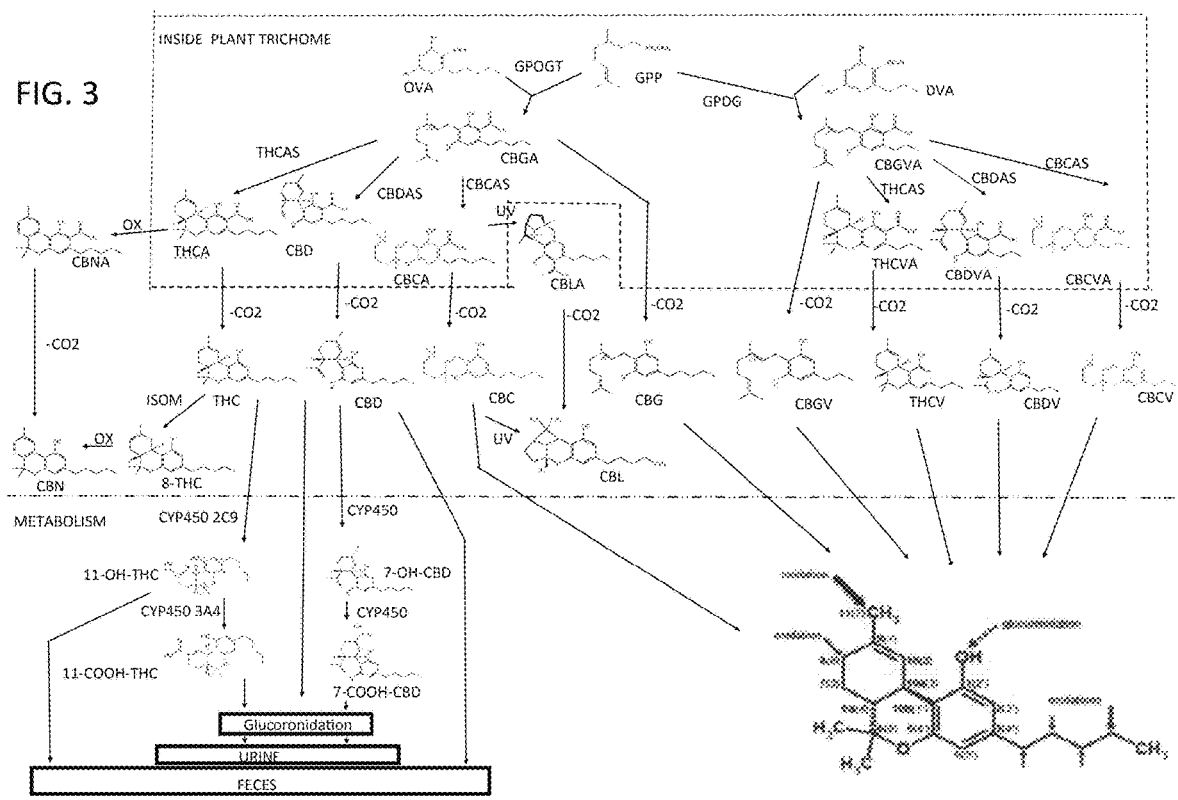
FIG. 3 shows a Map of cannabinoid synthesis, decarboxylation and metabolism FIG. 4 Legend for FIG. 3 Map of cannabinoid synthesis
Figure 6:
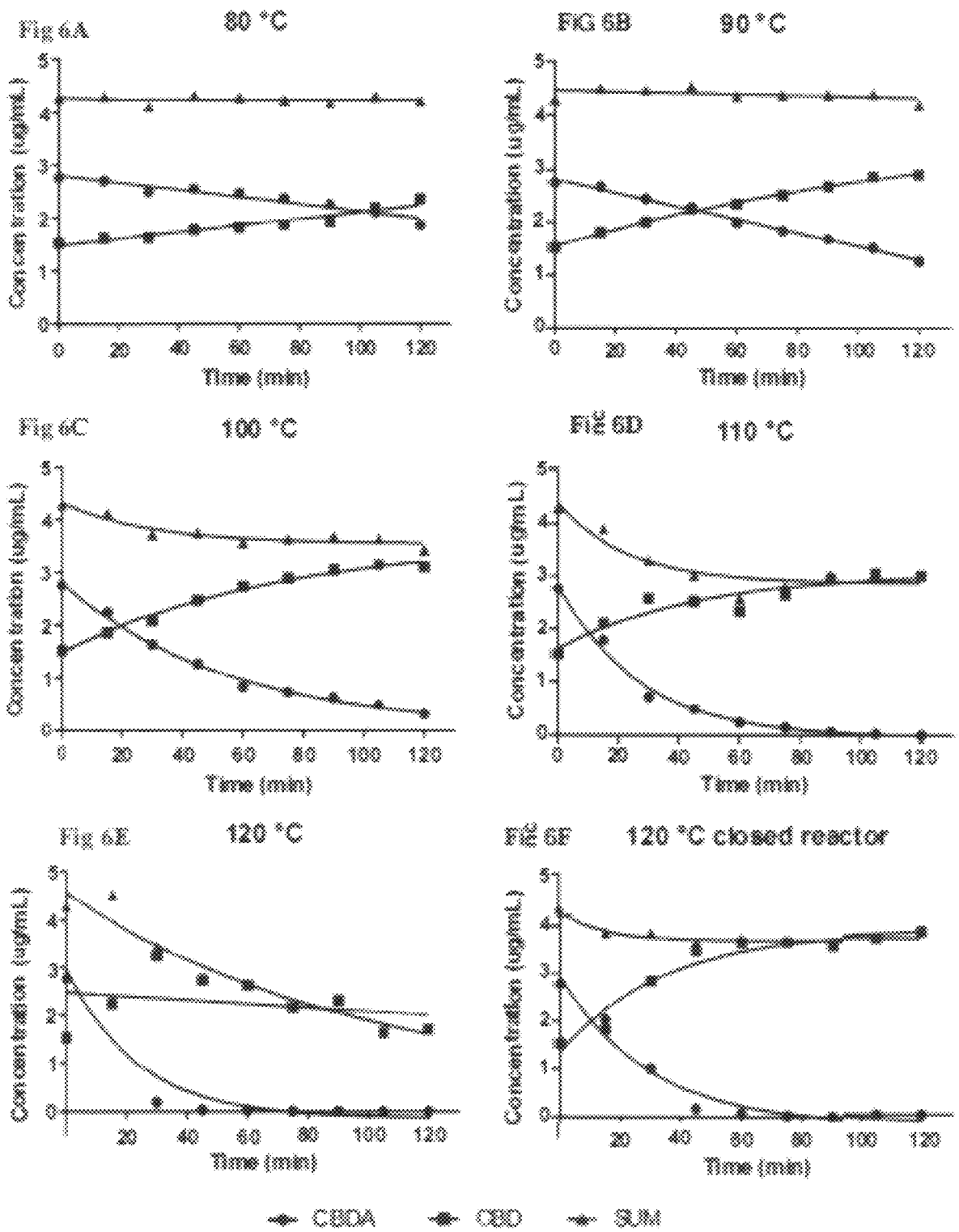
FIG. 6 shows CBD decarboxylation 80-120° C. in open and closed reactors
Figure 7:
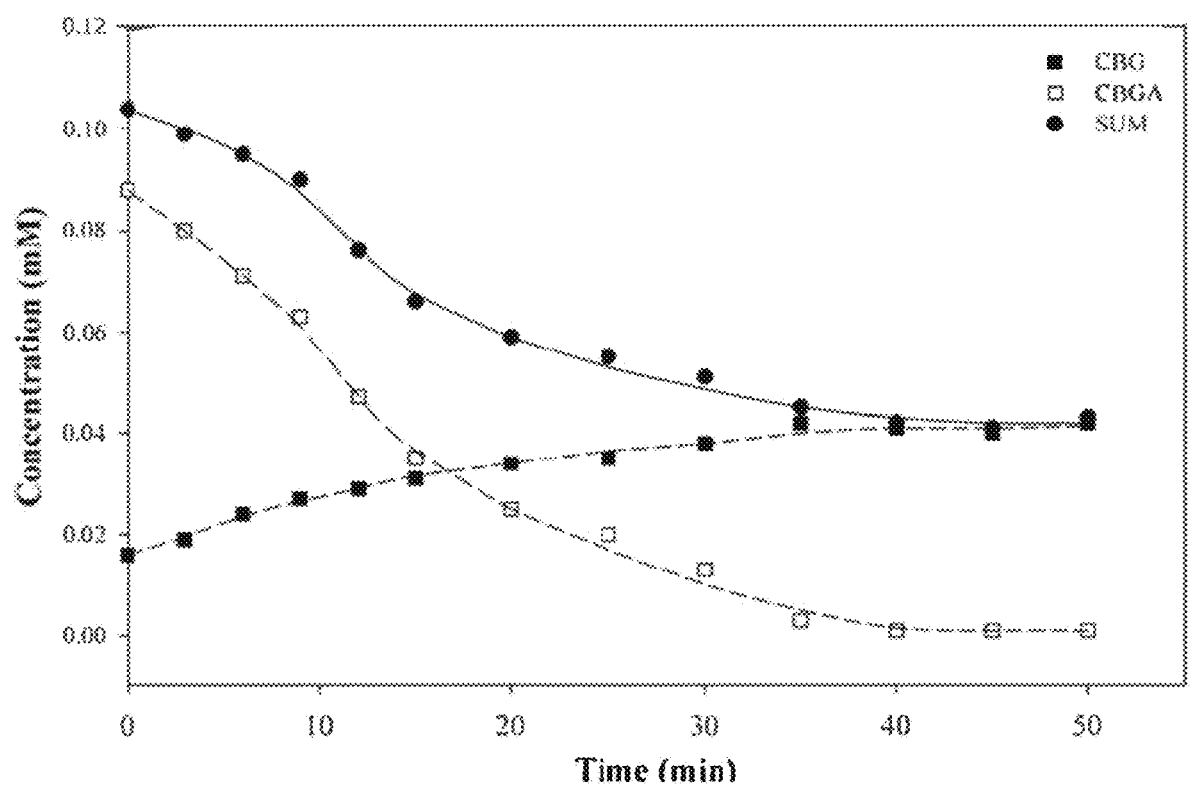
FIG. 7 shows CBG decarboxylation at 110° C.

10—heating plate
20—*cannabis* thin layer
30—metallic foil layer
40—parchment paper layer
50—perimeter pressure seal, flexible component
60—perimeter pressure seal, rigid component
70—port exit in heating plate
80—port through heating plate
90—water cooled condenser
92—tubing connecting heating plate port to watercooled condenser
102—hopper
104—upper conveyor belt
106—lower conveyor belt
107—roller
108—heated roller
110—scraper
112—receiver conveyor belt
120—roller
122—collector
200—heated plate
202—hinge
300—Station 1 inserting thin layer
302—Station 0 removing thin layer
303—heated hinged plates
308—rotating circular arrangement of heated hinged plates
400—belt
402—heated drum
404—heated outer surface of drum
406—scraper 408—roller
414—receiving trough
418—collector

DETAILED DESCRIPTION OF INVENTION

Education

Decarb

Decarboxylation converts acidic forms of cannabinoids to their neutral forms. For example THCA is converted by decarboxylation to THC. This occurs by heating. During the process there are competing degradation reactions.

The *cannabis* plant has been utilized by mankind for least 4000 years, when it was included in the first known written Chinese historical medical record. It seems likely its use dated from prehistory. The plant was known for its intoxicating effects. Its seeds were also used medicinally as well as for food.

The scope of medical *cannabis* use has expanded greatly in the last few decades. Most initial research focused on the single most active cannabinoid, namely THC. Therapeutic applications also focused on THC and found particularly effective application in nausea/vomiting, cachexia and appetite stimulation, and pain. The plant has always retained its demand as an intoxicant.

*Cannabis* contains a wealth of phytochemicals, the main pharmacologically active ones being cannabinoids, terpenes and flavonoids. Certain compounds when in the presence of others exert a synergistic effect in various pharmacological actions. It is well-known the cannabinoids have synergistic effects on one another, with terpenes having a synergistic effect on cannabinoids. The cannabinoid terpene interactions are typically referred to as the entourage effect. It might be expected that flavonoids can add to the effects of other compounds.

This multi-pronged effect of so many coexistent phytochemicals has been compared to a shotgun effect compared to isolated THC as the silver bullet in therapeutic use.

Psychoactivity

With more available knowledge about the non-psychoactive cannabinoids it is clear they have potential medical usefulness. With wider availability of high CBC and CBG content cultivars those families of cannabinoids can be included in a therapeutic prescription, based on knowledge of their usefulness.

In the THC family of cannabinoids from the precursor THCA to THC, 11OH THC, 11 OH nor 9 THC, Delta 8 THC, CBN A, and CBN, the majority of them have some psycho activity. CBD may exhibit some sedative properties.

In the other families of cannabinoids, namely CBC, CBG, THCV, CBDV, CBCV and CBGV, not them, i.e. the neutral moiety, nor their precursors or metabolites demonstrated psycho activity.

THC and CBD

As knowledge became more available regarding the non-psychoactive cannabinoids their therapeutic uses became evident. CBD due to its prevalence particularly in the hemp strains of *cannabis* was studied next. Laboratory models showed significant effects but widespread human studies have yet to be performed. Most significant was probably its synergistic and modulating effects with THC.

History of Use

The plant has mainly been smoked in its various forms, from dried plant material to hashish preparations, pressed or liquid. *Cannabis* tincture was in the US pharmacopeia until its prohibition. Plants were bred and extracts were optimized to produce high content THC, the main psychoactive ingredient and therefore desirable as an intoxicant. THC containing plants when smoked are psychoactive and generally referred to as marijuana. The second type of *cannabis* plant is called hemp, usually has a very low content of THC, but can have a high content of CBD, a non-intoxicating cannabinoid.

Raw Plant

To say THC containing plants is a misnomer, the plant produces the acidic partner to THC or THCA. Heat converts the THCA to THC during smoking making it available within the body. Actually all the cannabinoids exist within the plant after their production in the acidic form (e.g. THCA) except for a small amount that may have degraded to its neutral form (e.g. THC).

Therefore for example dried, unheated marijuana contains predominantly THCA as its main cannabinoid, with little THC present. CBDA is the main cannabinoid in hemp, with little CBD present.

Smoking the dried plant is still the most popular form of ingestion but vaporizing and inhaling the extracted oil, known as vaping has been gaining in popularity.

Current Medicinal Trends

Current practice in *cannabis* medicine has users trying different *cannabis* strains whether smoked or vaped for a effect on their medical condition. This is trial and error under the best of circumstances but necessitates a wide variety of cultivars and selective breeding which is time-consuming relative to an individual lifetime.

In initial studies in pain patients, synthetic THC provided analgesic effects, plant extracts containing similar THC concentration were found preferable. Further smoked whole plant *cannabis* also provided significant relief with less side effects than the purer, i.e. synthetic THC.

Synergy

This progression of efficacy and satisfaction from pure THC, to extracts to whole plant implies more available synergism from coexisting phytochemicals. The therapeutic effects may not be limited simply to analgesia but also the experience of pain. Further it may indicate improved efficacy and preference with the whole plant, not extract or synthetic.

Tea

A common form of medicinal *cannabis* in Europe is *cannabis* tea. Historically aqueous extracts of *cannabis* have not been popular since the desired effect was typically intoxication. Analysis of *cannabis* tea shows relatively high THCA and low THC. It appears the THC saturates at a concentration of about 10 mg/L. This puts it precisely in the range commonly used for many therapeutic indications. And conveniently this means an 8 ounce glass of tea would contain about 2.5 mg, again a commonly used dose, low enough to prevent intoxicating side effects.

One could expect similar low-level saturation of the other neutral cannabinoids in tea, again in the therapeutic range. Also one could expect significant extraction of other acidic cannabinoids other than THCA. Further, other hydrophilic compounds that would not be typically obtained in less polar *cannabis* extracts would also be soluble and available.

The prescriptive, custom *cannabis* as formulated here is easily incorporated into aqueous extracts such as tea. The neutral cannabinoids due to their low saturation concentration will "self regulate" in terms of producing a low dose. Acidic partners to the neutral cannabinoids should be in significantly higher concentrations. Precision Decarboxylation Precision Decarboxylation Some might be concerned about microbial contamination of the plant material when taking orally, the dry, not decarboxylated *cannabis*. While part of the sample analysis prior to clearing a specific harvest for sale, is for bacteria and fungus, concern may persist. High temperature decarboxylation also serves a sterilization process.

Figure 8:
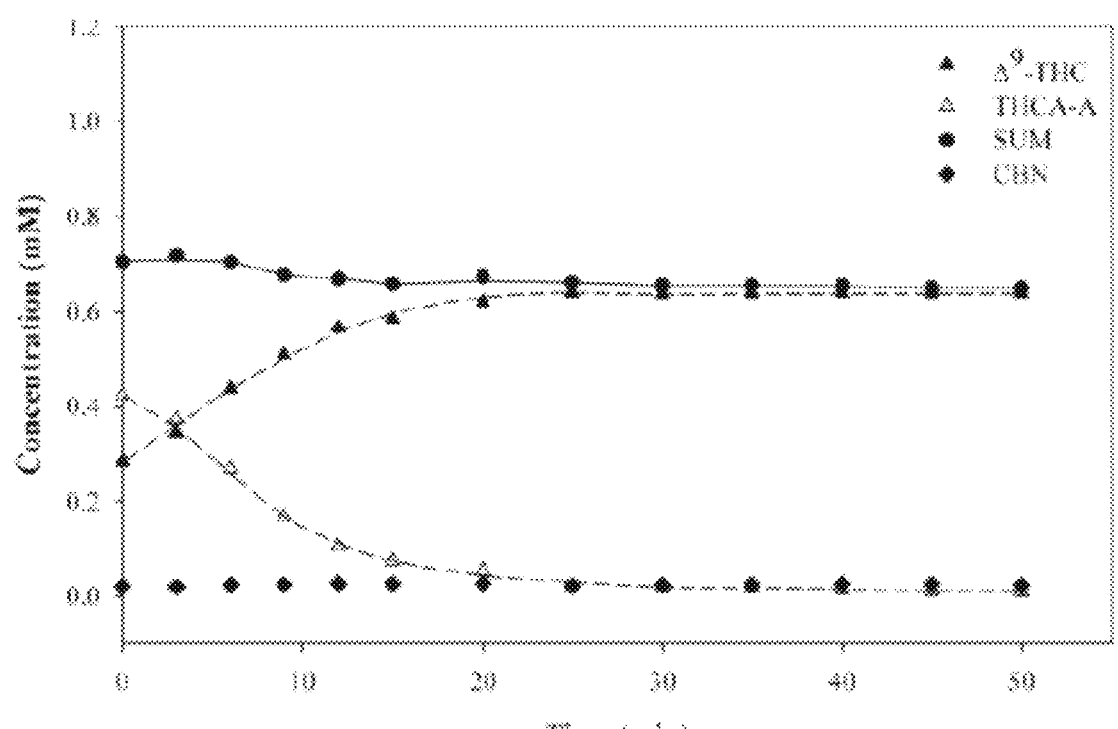
FIG. 8 shows THCA, THC, CBN during decarboxylation at 110° C.

The ratio of a neutral to acidic cannabinoid can also be predicted in a given apparatus through observing the concentration curves of the acidic and neutral component during the decarboxylation process. FIG. 8. At time zero the acidic compound will be at its highest concentration. This will decrease until complete conversion when the concentration will go to zero. Conversely at time zero the neutral component will be at its lowest concentration, essentially zero. Over time at the particular temperature the concentration of the neutral component will increase until it reaches its maximum.

The concentrations are plotted stoichiometrically, i.e. by molar concentration. The curves are normalized so the final concentration of the product is normalized to one in the final concentration of the substrate is zero.

Starting from time zero following the time course it soon reaches a time point where the curves intersect. Since the points are plotted by molar concentration, this crossing indicates an equimolar concentration of the acidic and neutral forms. This is truly a one to one relationship compared to the one: one ratio by milligrams.

Therefore a one-to-one molar concentration is predictable by the conversion curve. This curve will be specific to the particular apparatus used and there may be significant variation between apparatuses, with varying predictive times. Other molar ratios can also be predicted from the curves. For precise and accurate predictability a precisely controlled decarboxylation method is necessary such as a thin layer technique.

The equimolar or equal weight prediction can also be made from the corresponding peak time at that temperature. The amount of heated product at the peak is noted. The time on the graph where the concentration of the product is one half of the peak concentration is noted. This is the time at which one half of the conversion will have completed and the amounts of acidic and neutral components are equal stoichiometrically plotted as molarity or by weight if measured and plotted by weight.

Thus a custom *cannabis* product can be generated with predictable cannabinoid content, particularly with prescribed molar ratios. Percent by weight is also tracked if it is desirable to have a 1 to 1 mg ratio while blending.

Steam

The thin layer decarboxylation process proceeds through at least two phases. In the first phase any remaining water content is rapidly vaporized to steam. The higher the temperature of the more rapidly this phase completes. The steaming process is coincident with significant vaporization of terpenes. As the steam is released it carries the terpenes effectively acts as a steam distillation.

In another embodiment this terpene steam, in a similar fashion to a vaporizer, i.e. using an air source to condition the air in terms of heat and concentration, then inhaled. Or the vapor is captured in a collapsible bag, to be inhaled from by the user.

Figure 9:
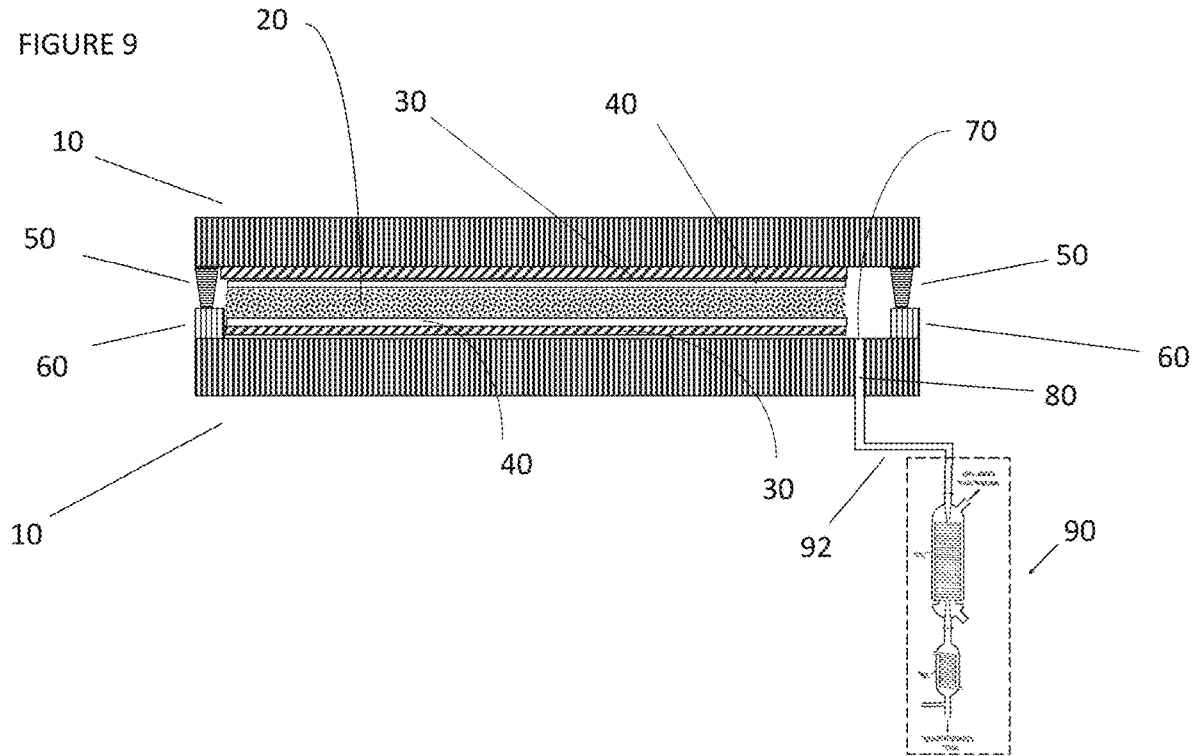
FIG. 9 shows Sectional view of plates illustrating ported vent configured for steam/terpene distillation FIG. 10 Shows lateral view of automated conveyor decarboxylator FIG. 11 Shows lateral view of conveyor belt with hinged plates configuration

Alternately the heating plates in a thin layer decarboxylator can be sealed at the perimeter 50 and 60 sufficient to contain vacuum or pressure. FIG. 9. Then one or more ports 70 into the thin layer chamber through the heating plate, are ported 92 externally, optionally under vacuum. During the decarboxylation process the port 92 directs any water vapor or further vaporization of cannabinoids or terpenes to an external condenser 90, ideally fractionally distilling the water vapor from oils. The amount of oil produced will be proportional to the amount of *cannabis* processed.

When a sufficient amount of oil is collected it can be reapplied to the decarboxylated *cannabis*. This recaptures the majority of cannabinoids and terpenes volatilize during the decarboxylation step.

Commercial/Automated

To use the method on a commercial scale the same principles are applied, namely a thin layer of material caught in contact between two heated flat surfaces, (or a nonheated flat surface pressing the material sufficiently to contact a heated flat surface). Automated methods may be preferable. Precise temperature control is desirable in all embodiments for the predictive conversion values to be accurate and to minimize waste. Smart temperature control is implemented to avoid errors in conversion control, mainly to ensure adequate thermal input for complete conversion if desired or optionally a partial decarboxylation.

Figure 10:
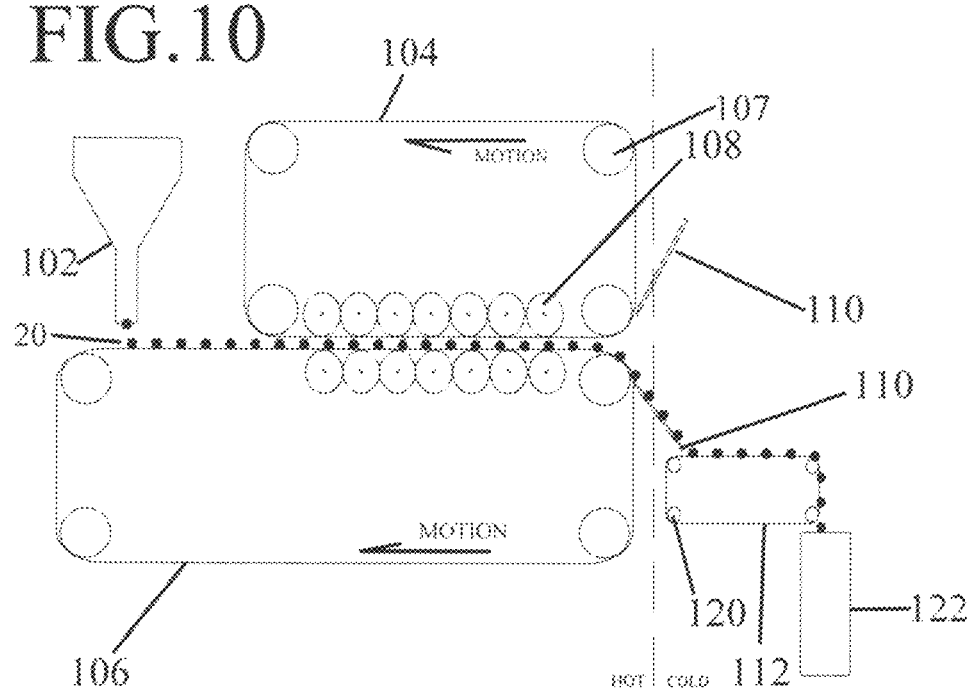

An embodiment is a horizontal conveyor, FIG. 10 with either heated belts 104 and 106 or heated rollers 108 to maintain the working temperature. An opposing conveyor 104 positioned for the flat surface of its belt to run opposed and in contact with the lower conveyor. Again, the heat may be in either or both heated contact surfaces, preferably both. A hopper 102 dispenses over the bottom belt 106 forming the continuous thin layer 20 as the belt moves beneath it at a constant speed.

Figure 11:
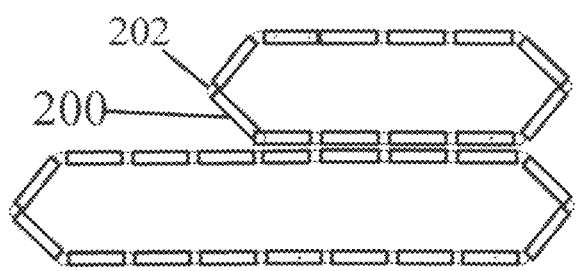

An embodiment is to have the opposed heated surfaces instead of belts utilize a looped series of chained heated plates FIG. 11. The heated plates 200 are daisychained via the hinges 202. With two opposing loops, two opposing plates would meet and contact as a thin layer is inserted between the plates. The conveyor continues for the predetermined time which is linked to the speed of the conveyor.

Figure 12:
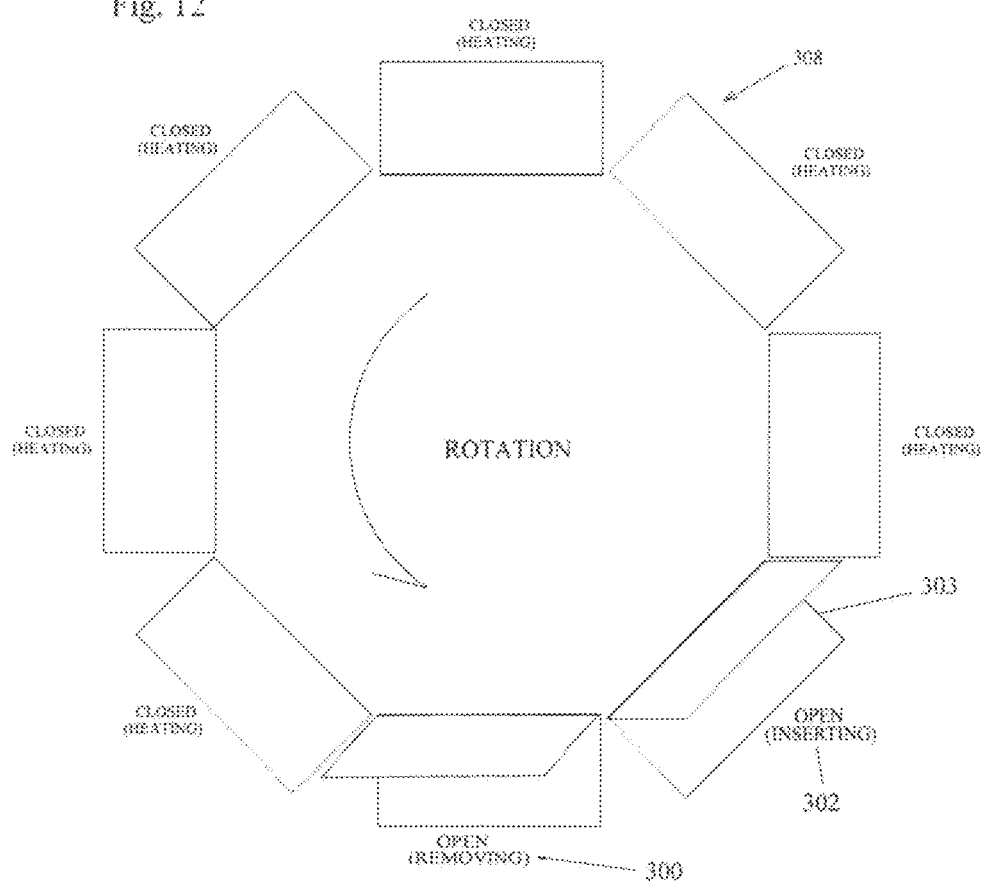
FIG. 12 shows overhead view of revolving hinged plates configuration

An embodiment or configuration would be a series of heated flat hinged plates surfaces like panini presses 302. FIG. 12. These can be linked to travel along a horizontal loop, the looping time controlled for the decarboxylation or chemical conversion. As the system indexes in a circle, stationary positions 300 and 302 adjacent to the moving hinged plates would be controlled to insert prefolded packets or material, removing the packets or material at another station. Again immediate chilling of the product is desirable.

Figure 13:
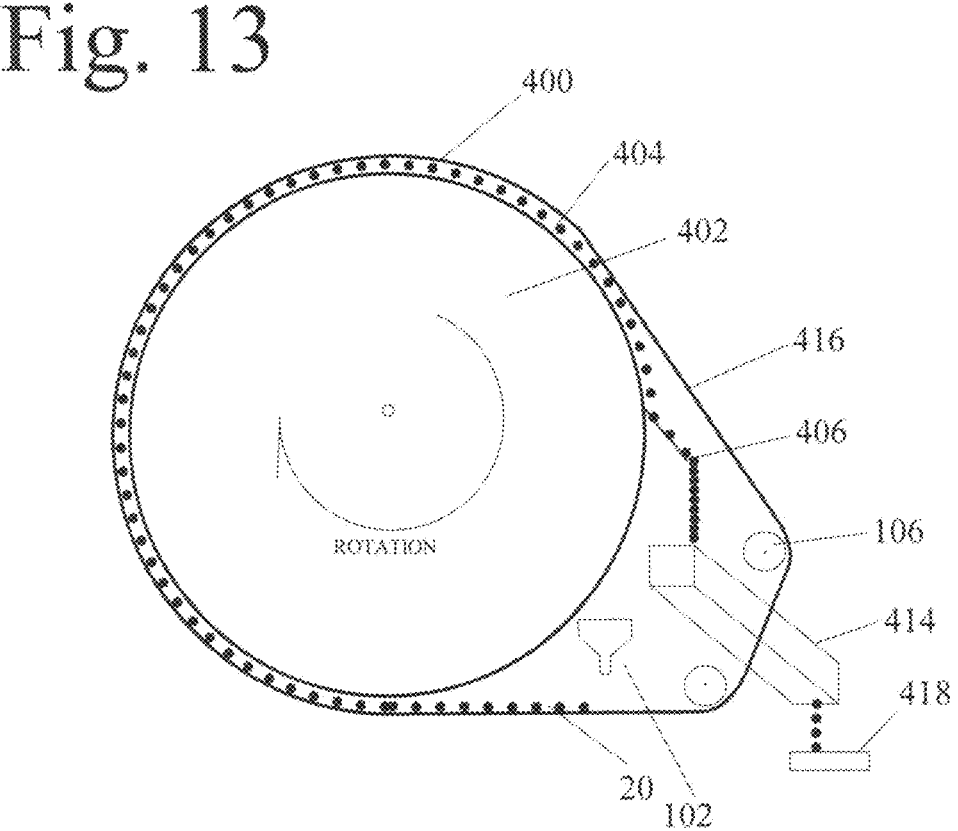
FIG. 13 shows lateral view of revolving drum reactor

Another embodiment is made similar to a photographic print dryer. FIG. 13. A large heated drum 402 is slowly rotate about its axis and a continuous belt 400 contacts it following the drum surface 404. A thin layer of *cannabis* 20 is deposited on the belt 404 by the hopper 102, then the belt 400 holds the thin layer 20 in contact with the heated drum 402 and follows it. The duration of contact is predetermined from known data. The conversion is partial or complete as desired. As the thin layer 20 comes off the drum assisted by a scraper 406 and is transported away via a collecting trough 414 into a collector 418, it is preferably immediately chilled as previously. The belt 400 can contain an integral electrical coil or other heating means to have a heated belt. This allows two sided heating, a more effective, faster and predictable method. The belt 400 should also be gas impermeable to minimize loss of compound to vaporization and escape from the system.

Cannabinoids

Cannabinoids in dried *cannabis* exist predominantly in their acidic form. Neutral forms exist in trace amounts in dried *cannabis*. After decarboxylation all the acidic cannabinoids are converted to their neutral forms.

For example a *Cannabis sativa* plant cultivated for psychoactive THC at maturity will contain predominantly THCA. When the dried plant is heated under appropriate conditions of time and temperature, THCA is decarboxylated and becomes THC. Under appropriate conditions the conversion should be about 95% and for purposes here can be assumed to approximate 100%.

Similarly other acidic cannabinoid forms are decarboxylated to their neutral forms under appropriate time and temperature conditions specific for that cannabinoid pair. These acidic/neutral couples include CBDA/CBD, CBGA/CBG, CBCA/CBC, THCVA/THCV, CBDVA/CBDV, CBCVA/CBCV and CBGVA/CBGV.

THC, (Delta-9 THC Unless Specified))

MW 314.2 g per mole BP 157° C. 315° F. Decarboxylation product of THCA. Synergistic with limonene, pinene, linalool, caryophyllene. Partial agonist of the CB one and CB two receptors of the endocannabinoid system. Its actions are analogous to the endocannabinoid AEA.

Actions: psychoactive, antifungal, antibacterial, anticancer, appetite stimulant, analgesic, muscle relaxant, antispasmodic, bronchodilator, neuroprotective antioxidant, antipruritic agent in jaundice, anti-inflammatory with 20 times the activity of aspirin and two times the activity of hydrocortisone.

Indications: decrease Alzheimer's symptoms, benefit an duodenal ulcers, nerve related pain, diabetic neuropathy, pain of multiple sclerosis, PTSD, nausea and vomiting associated with chemotherapy, wasting syndrome associated with cancer and HIV, effects to decrease eye pressure may benefit glaucoma. Insomnia, sleep apnea, nightmares, inflammatory bowel disease including Crohn's, ulcerative colitis and leaky gut syndrome, adjunctive analgesic in advanced cancer, Parkinson's. In cancer combination effect noted with THC plus CBD plus CBG plus CBC.

THCA

MW 358.4 g per mole. BP 105° C. 220° F. Produced by enzyme catalyzed reaction of CBGA. Decarboxylated by heating and drying to THC. Therefore not available by smoking or vaporization as decarboxylation rapidly occurs. Causes cell death via apoptosis in suspension culture.

Actions: anti-inflammatory, neuroprotective, anti-emetic, antiproliferative, anticancer, antispasmodic, insecticidal.

Indications: arthritis, lupus, Alzheimer's, Parkinson's, cancer.

CBGA

Causes cell death via apoptosis in suspension culture. Produces necrosis in plant cells, usually not problematic as the compound is sequestered in the trichomes.

Actions: insecticidal, cancer, analgesic, anti-inflammatory.

CBG

MW 316.4. Produced by the decarboxylation of CBGA. Synergistic with phytol, pinene, linalool, caryophyllene oxide, limonene. New chemo types being developed lacking downstream enzyme expressions, expressing all CBGA as their predominant cannabinoid.

Actions: modest antifungal, partial agonist at CB one and CB two receptors, insecticidal, analgesic, GABA uptake inhibitor greater than CBD or THC, muscle relaxant, analgesic, potent alpha-2 adrenal receptor agonist, anti-erythema, Lipo oxygenase blocker, cytotoxic to human epithelial and carcinoma at high doses, breast cancer, mildly antihypertensive, inhibits keratinocyte production, AEA uptake inhibitor, antimicrobial, strong activity against Mrsa, antidepressant (moderate 5HT1a antagonist).

Indications: cancer especially breast and prostate.

Delta 8 THC

MW 314.4 g per mole. Isomerization product of Delta nine THC. Psychoactive, less so than Delta nine THC, though notably no psychoactive effect in two—13-year-olds in one study.

Actions: anti-anxiety, antiemetic, neuroprotective, appetite stimulant greater than Delta 9 THC.

CBNA

MW 359.4. Degradative product of THCA. Scant literature on CBNA. Anti-inflammatory.

CBN

MW 310.1 BP 185° C. 365° F. Synergistic with nerodilol, myrcene, pinene, linalool, limonene. Oxidative byproduct of THC via Delta 8 THC. Psychoactive with 2 fold lower affinity for CB one receptor and 3 fold higher affinity for CB 2 receptor than THC. Approximately 10% activity of 9 THC.

Actions: potentiates THC, increases FSH, increases production of testicular testosterone, anticonvulsant, anti-inflammatory, analgesic, stimulates mesenchymal stem cells in bone marrow i.e., bone stimulant, antimicrobial against Mrsa, releases endorphins useful in pain, modulates thymocytes, appetite stimulant, most potent sedative for single cannabinoid, lowers ocular pressure.

indications: with THC for glaucoma, pain, may delay onset and relieve symptoms of degenerative motoric neural diseases such as ALS and MS, antibiotic for Mrsa.

CBDA

MW 358.2 g per mole. Produced enzymatically from CBGA substrate within the plant. Causes necrosis in plant cells, typically sequestered in the trichomes. Decarboxylated by heat and drying. Not available via smoking or vaporizing due to decarboxylation.

Actions: antibacterial, antiemetic, anti-inflammatory, antiproliferative, anticancer.

Noted to be a very potent antinausea compound but not commonly available. Actually is readily available in the non-decarboxylated plant.

CBD

MW 314.2 g per mole BP 180° C. 356° F. Decarboxylation product of CBDA. Synergistic with limonene, linalool, pinene, caryophyllene. Low binding affinity for CB one receptor. Antagonizes CB 1 receptor at low concentrations in presence of THC. Modulatory effect on THC associated adverse effects, short-term memory impairment, alertness, anxiety, tachycardia, hunger, social isolation. Bell shaped dose response curve, suggesting dose is a key factor.

Actions: sedation, antifungal, neuroprotective antioxidant more potent than tocopherol or ascorbate, anticonvulsant, antinausea, cytotoxic on breast cancer and many other cell lines while maintaining cyto preservation on normal cells, antimicrobial against Mrsa, 5 HT 1 a agonist, anti-anxiety, reduces stroke risk, atypical antipsychotic in schizophrenia, decreases social isolation induced by THC, analgesic, anti-inflammatory, antioxidant pro-apoptotic, anti-depression, antibacterial, anticancer anticonvulsive, antiemetic, anti-insomnia, anti-ischemic, bone stimulant, immunosuppressive, neuroprotective, serotonin uptake inhibitor, enhances norepinephrine activity, protects neurons from glutamate toxicity, acts synergistically with THC to reduce intestinal motility, anti overdose action against THC.

Uses: cancer pain in combination with THC, addiction, acne, anxiety, psychosis, movement disorders, neuropathic pain, cancer, and affective disorders, neurodegenerative disease, ischemia, nicotine addiction, osteoporosis, diabetes, OCD, lupus, Parkinson's, motor disorders, neuropathic pain, chronic pain, inflammatory arthritis, sedation, inflammatory bowel disease

CBDV

Actions: anticonvulsive, bone stimulant.

CBG

Decarboxylated CBGA. Usually unavailable in plant as CBGA consumed in cannabinoid production. Dry CBGA plant can be decarboxylated to produce CBG as with other acidic cannabinoids. Slight affinity for CB 1 receptor, similar to CBD.

Actions: antiproliferative, antibacterial against gram-positive, mycobacteria and fungi (greater than THC, CBD, CBC). Amantadine reuptake inhibitor. Inhibits LOX greater than THC. Inhibits erythema much greater than THC. Analgesic greater than THC.

Inhibits growth of human oral epithelioid carcinoma cells. Antidepressant, antifungal and bone stimulant.

CBGA

MW 360.4 g per mole. Synthesized enzymatically within the plant. Source of all cannabinoids. More common in hemp. High affinity alpha-2 adrenergic receptor agonist. 5 HT 1 a antagonist, low affinity CB 1 agonist. Antibiotic greater potency than CBN, similar to CBD.

Actions: analgesic greater than THC, antidepressant, mood stabilizer, prevents GABA uptake, increases brain serotonin, decreases ocular pressure.

Uses: psoriasis, eczema, glaucoma.

CBCA

MW 358.2. Enzymatic product of CBGA substrate. Causes necrosis in plant cells, usually sequestered in trichomes. Maximum production earlier in plant cycle.

Uses: antifungal, anti-inflammatory.

CBC

MW 314.2 grams per mole BP 220° C. 428° F. Decarboxylation product of CBCA. Synergistic with caryophyllene oxide and limonene. Found in freshly harvested, mostly tropical strains. Also being sourced with a cold water extraction of immature leaf matter from selectively bred chemo types.

Actions: anti-inflammatory synergistic with THC, analgesic, antibiotic stronger than THC and CBD, mild antifungal, cytotoxic in cancer cell lines, strong AEA uptake inhibitor, antibacterial, analgesic, anti-tumor of the breast more effective with CBD, THC and CBG, antidepressant, antiviral, promotes brain neurogenesis with increased cell numbers, improves memory and learning, offsets some dementias, anti-insomnia and bone stimulant.

THCV actions: anticonvulsive, appetite suppressant, bone stimulant, neuroprotective.

uses: anti-inflammatory

CBLA

MW 358.2. Most stable cannabinoid to heat, resistant to decarboxylation. Yields little CBL on heating. Converts by UV light.

uses: anti-inflammatory and antitumor

CBL

MW 314.2. Produced from CBC by UV light. Unknown properties.

Terpenes

Most of the terpenes are colorless, fragrant liquids which are lighter than water and volatile with steam. A few of them are solids e.g. camphor. All are soluble in organic solvent and usually insoluble in water.

They are open chain or cyclic unsaturated compounds having one or more double bonds. Consequently, they undergo addition reactions with hydrogen, halogen, acids etc. A number of addition products have antiseptic properties.

They undergo polymerization and dehydrogenation.

They are easily oxidized nearly by all the oxidizing agents. On thermal decomposition, most of the turbine noise yields isoprene as one of the products.

Terpenes are a group of naturally occurring compounds the majority of which occur in plants. Terpinoids are volatile substances which give plants and flowers their fragrance.

TEPRENES % indicates percent by weight of total terpenes

Beta Caryophyllene 2.3-3.6% found in cloves, Thai basil, cinnamon, black pepper, oregano, balsam, green leafy vegetables.

Predominant terpene in extracts of decarboxylated *cannabis*.

Full CB two agonist.

Actions: anti-inflammatory PG one pathway, comparable in potency to phenylbutazone. In combination with eugenol equivalent to a etodolac and indomethacin, anxiolytic, antidepressant, anticancer, local anesthetic, anti-nociceptive, anti overdose action against THC.

Uses: gastric cytoprotective effect, treatment of duodenal ulcer in UK

Bisabolol found in candeia shrub and German chamomile.

Actions: anti-inflammatory, wound healing properties, antimycotic inhibits *Candida*, antibacterial against gram-positive Borneol found in rosemary, thyme, cinnamon, walnut oil.

Oxidized to camphor.

Actions: calming sedative, anti-inflammatory, to alleviate fatigue and stress, anti-nociceptive, analgesic, local anesthetic, antiseptic, digestive aid, sedative, anti-spasmodic, reduce pain and swelling, bronchodilator, cough suppressant.

Camphene 0.1-1.1% found in turpentine, Cyprus, neroli, Valerian, camphor, citronella, Ginger

Actions: antioxidant, anti-inflammatory, antibiotic, may reduce cholesterol and triglycerides Camphor found in rosemary leaves, camphor basal, camphor tree, kapur tree, camphor laurel actions: readily absorbed through skin, cooling sensation, slight local anesthetic, antimicrobial, cough suppressant, decongestant, skin vasodilator, reduces appetite, increases heart rate, antifungal, antiplatelet aggregation properties.

uses: for pain, itching, swelling, sprains, inflammation, fevers, fatigue.

Caryophyllene Oxide 1.33-1.58% found in *Eucalyptus*, lemon balm, Melaleucaactions: in plant is insecticidal, anti-feedant, broad-spectrum antifungal, antiplatelet aggregation Uses: clinical onychomycosis efficacy similar to cyclopiroxolamine and sulconazole, effective in 15 days at 8% concentration.

Carene 0.1-2.5% found in Cypress oil, juniper berry oil, fir needle oil, Pine/Cedar resin, bell pepper, basil, grapefruit, orange, citrus peel oil of lemons, limes, Mandarin, tangerines, kumquats. Non-toxic but may cause coughing and itchy throat as irritates when inhaled, Actions: anti-inflammatory, when concentrated may be CN S depressant or skin irritant Cedrene found in fenugreek and Cedar.

Actions: antiseptic, antimicrobial, antifungal, anticancer especially T cell lymphoma.

Cymene found in cumin, thyme, anise, coriander, Mace, oregano, *Eucalyptus, Angelica*, bay leaf, basil, carrot seed, cloves, Sage, grapefruit oil actions: acetylcholinesterase inhibitor, antibacterial, antifungal, anti-inflammatory, anti-nociceptive, analgesic Eucalyptol found in camphor laurel, bay leaf, tea tree, mugwort, sweet basil, wormwood, rosemary, common Sage actions: analgesic, cough suppressant, antifungal, anti-inflammatory uses: reduces airway mucus hyper secretions in asthma, non-purulent rhinosinusitis.

Fenchol found in basil, fennel, nutmeg, Pine, rosemary oil, lime oil, beer actions: acetylcholinesterase inhibitor, antibacterial Geraniol found in rose, geranium, lime, lemon, lemongrass, nutmeg, bergamot, carrot, coriander, lavender, blueberry, blackberry, tobacco Actions: antioxidant, inhibits growth of colon cancer, mosquito repellent Geranyl Acetate found in citronella, palmarosa, geranium, coriander, neroli, lemongrass, petite grain, carrot, *Sassafras*, rose Actions: antimicrobial, antifungal, anti-inflammatory Guiaol found in guiacum, Cyprus plant Actions: antimicrobial, anti-inflammatory, laxative, diuretic, insecticidal Uses: cough, constipation, arthritis Humulene 6.97-8.71% found in hops, Vietnamese coriander, Pine tree, orange tree, marsh elder, tobacco, Sage, *ginseng*, Ginger, sunflower Isomer of caryophyllene.

Actions: antitumor, antibacterial, anti-inflammatory with caryophyllene, anorectic Iso Borneol found in mugwort Actions: antiviral (HSV inhibitor), antioxidant, anti-inflammatory, antimicrobial Isopulegol found in corn mint, Penny Royal, lemongrass, geranium. Precursor to menthol.

Actions: Gastro protective, anti-convulsive, anti-inflammatory, antioxidant

Limonene 1.2-21.1% found in lemon, citrus rinds, juniper, peppermint actions: highly absorbed by inhalation, P4 50 2B1 inhibitor, antifungal and antibacterial, blocks carcinogenesis induces differentiation and induces apoptosis, protective against lung, liver, pancreas and skin cancers, acetylcholinesterase inhibitor, assist absorption of other terpenes through skin, antidepressant when inhaled general uplift in mood and attitude, helps promote weight loss, antioxidant, radical scavenger, improves fatty liver induced by diet, increases low blood pressure, anxiolytic, anti-dermatophyte, decrease morphine dosage when inhaled post surgically, anti overdose action against THC.

Linalool found in lavender, bay laurel, sweet basil, mint, cinnamon, citrus, rose, neroli oil Actions: sedative/sedating synergistic with neroli, mitigates anxiety of THC, antidepressant, anxiolytic, local anesthetic equivalent to procaine and menthol, alleviate skin burns without scarring, anti-Leishmanial agent, anti-inflammatory, immune booster, may reduce inflammation caused by cigarette smoke, calming, relaxing, mood lifting, reduce headaches and migraine by affecting GABA and glutamate systems acts as sedative, anxiolytic and anticonvulsant.

Uses: Alzheimer's, insomnia.

Menthol found in corn mint, peppermint actions: vasodilation, speeding healing, kappa opioid receptor may produce numbing, analgesic topical, anti-inflammatory, menthol cigarettes claimed to have lower cancer risk the non-menthol.

Uses: arthritis, bursitis, tendinitis muscle spasm/strains, C, bone pain, bruising, cramping.

Myrcene 16.1-80.1% found in menthol, lemongrass, hemp actions: potent analgesic acting at central sites antagonized by naloxone, reduces inflammation peripherally blocks inflammatory activity of prostaglandin E2 similar to CBD, CBC, CBG, sedative/relaxing used as a sleep aid in Germany, lowers resistance across blood brain barrier, increases cell membrane permeability allowing cannabinoids and terpenes to take quick effect, antimicrobial, antiseptic, antidepressant, anti-carcinogenic, anti-inflammatory, analgesic, anti-mutagenic, inhibits gastric/duodenal ulcers, increases maximum saturation level of CB one receptors increasing maximal psychoactive effect, increases sedative effect of THC, inhibits P4 502 B1 prevents activation of pro-mutagen which is extremely hepatotoxic and carcinogenic.

Nerolidol found in neroli, citrus peels, Ginger, Jasmine, lavender, tea tree, citronella, lemongrass, brasserola orchid.

Actions: sedative, antifungal, enhances skin penetration for transdermal delivery, anti-protozoal, antimalarial, anti-leishmaniasis.

Ocimene 0.1-18.7% found in mint, parsley, pepper, basil, mangoes, orchids, kumquats, allspice

Actions: antiviral, antifungal, antiseptic, decongestant, antibacterial

Phellanderene 0.3-2.8% found in allspice, cinnamon, dill, garlic, pepper, parsley, oils including *Angelica, Eucalyptus*, lavender, mentha, fennel, Ginger, turmeric, *Pinus* species.

Actions: antifungal, antidepressant,

Uses: used in Chinese medicine for digestive disorders

Phytol found in green tea and wild lettuce.

Breakdown product of chlorophyll and tocopherol.

Actions: increased GABA expression by inhibiting degradative enzymes may explain its relaxing effects, prevented vitamin a induced teratogenesis, useful in regulating blood glucose, reducing blood pressure and reducing cholesterol Pulegone found in catnip, peppermint, spearmint, Penny Royal, rosemary actions: may eliminate short-term memory consolidation from THC, acetylcholinesterase inhibitor, mucolytic, sedative Pinene 0.5-46.3% found in conifers and pine needles.

Actions: P4 50 2B1 inhibitor, anti-inflammatory via PGE one pathway, acetylcholinesterase inhibitor, antibiotic effective against *S aureus S epidermis* and *P acne*, in vitro cytotoxicity against human hepatocellular carcinoma and human melanoma, benefits memory, antitumor, anticancer, expectorant, bronchodilator, local antiseptic, counteracts THC anxiety and memory loss, may counteract THC induced intoxication, anti overdose action against THC.

Sabinene 0.1-0.3% found in Norway spruce, black pepper, basil, nutmeg actions: antioxidant, anti-inflammatory uses: relieves arthritis, improves digestion, benefits liver function Terpinene 0.1-18% found in citrus fruits actions: P4 52 B1 inhibitor, acetylcholinesterase inhibitor, strong antioxidant Terpeneol found in lilacs, pine trees, lime blossoms, *Eucalyptus*, labsong souchong tea, actions: acetylcholinesterase inhibitor, antibiotic effective against *aureus S epidermis* and *P acne*, calming, relaxing, mild sedative, inhibits acne, anti-inflammatory, antioxidant, antimalarial, anticancer kill still worse directly Terpinolene 0.1-41.8% found in nutmeg, tea tree, conifers, citrus, apples, cumin, marjoram, Sage, Rosemary, Monterey cypress and lilacs actions: CNS depressant induces drowsiness and sleep, reduces psychological excitement, sedative effect when inhaled, anticancer, antioxidant, antibacterial, antifungal, anti-proliferative uses: insomnia, anxiety Valencene found in Valencia orangesactions: anti-inflammatory, insecticidal stronger and less toxic than DEET Ratios Commercial formulations of extracts use varying ratios of THC to CBD for desired goals. A THC: CBD ratio of 1:1 is common. Typical dispensary extracts go from the 1:1 ratio and increase the CBD to not uncommonly 1:20. Generally CBD is not reduced below the THC level. For precision ratios blending of oils is used.

| CA 256-8997 extract, synthetic | CBD:THC 1:1 | rheumatoid | five-25 mg daily |
| --- | --- | --- | --- |
|  | 0.93:1 | pain, inflammation, sleep | 5-25 mg daily |
| EP 214-6731 extract | CBD, CBG, CBDA | prostate cancer |  |
| EP 244-8637 extract | CBD 400-800 mg | Epilepsy | plus/minus THCV greater than 1.5 mg |
| US 201-003-5978 extract, pure, synthetic | THC/CBD 0.93:1 | Peripheral neuropathic pain | five-25 mg each |

| US 796-8594 | THC:CBD 0.93:1 | Cancer pain with constipation | five-25 mg each maximum less than or equal to 120 mg CBD, 130 mg THC |
| --- | --- | --- | --- |
| EP 203-7902 GB 237-7633 | CBD:THC 24:1 CBD:THC greater than 2.5:1 | Neuropathic pain pharmaceutical composition | plus minus THCV greater than 1.5:1-CBDV, CBDV greater than THCV 9:1 |

Operation HPLC Analysis

Homogenized plant material was prepared to maintain a uniform consistency and chemical uniformity. Two hundred mg aliquots of the homogenized plant material were sprinkled in a fine layer onto a thin piece of metal foil, which was folded over, enclosing the sample in a flat thin manner.

The sample was placed between flat metal plates preheated to the working temperature. The temperature was monitored and maintained to within one degree via a PID controller. Heating apparatus used was a commercial 1000 W panini press with flat plates, FIG. 18. The PID controller was an Auburn Instruments WSD-1501GPH.

On removal from the heat, the sample is immediately cooled to <32 F to stop the reactions. After several minutes cooling, 100 mg of the sample material is stirred constantly for 5 min in 95% ethanol. The supernatant is immediately filtered through a 0.22 um PTFE filter. The sample is further diluted 10:1 in ethanol.

Ten ul of the diluted sample extract is injected for analysis in a reverse phase HPLC system. The system consists of Waters 717 autoinjector, Waters 600 pump and controller, monitored with a Waters 486 variable wavelength absorbance detector. Typical analysis was run at 220 nm. CBN formation was also monitored at 290 nm. Data was collected via a Kipp-Zonen chart recorder.

The column is a Waters C18 3.5 um 4.6×75 mm Assymetry column. Isocratic mobile phase of 75% ETOH/25% H2O, containing 2.0 g ammonium acetate/L at 0.5 ml/min flow rate, temp 27 C, resulted in back pressure of 800-1000 psi, good separation of all compounds of interest and a run time of 10 min.

Decarboxylation

Steps

Dried *cannabis* flowers are pulverized or very finely chopped, after being cleaned of stem material. The pulverized material is then spread in a thin layer, preferably ⅛" or less onto a controllably heatable surface. A second, similarly controllably heatable surface is applied to the exposed top of the thin layer of material. The pressure of the contact is a function of the weight of the upper contacting surface embodiment. No additional pressure is applied. The heating period is determined by the material of interest, here THC or CBD. The desired time can be determined from FIGS. 14 and 15.

The material is then rapidly removed and immediately chilled to <32 F. A flat, chilled surface in a freezer is suitable. Again, a second cooling surface may be applied to the opposite of the chilling material.

Packet

Figure 16:
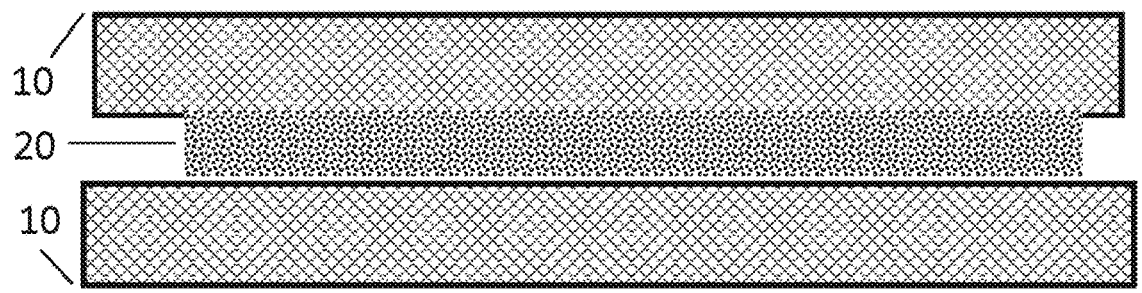
FIG. 16A shows thin layer directly on heating plates
FIG. 16B shows thin layer contained between aluminum foil layers FIG. 16 C shows thin layer contained between parchment layers which is further contained between aluminum foil layers.
Figure 16:
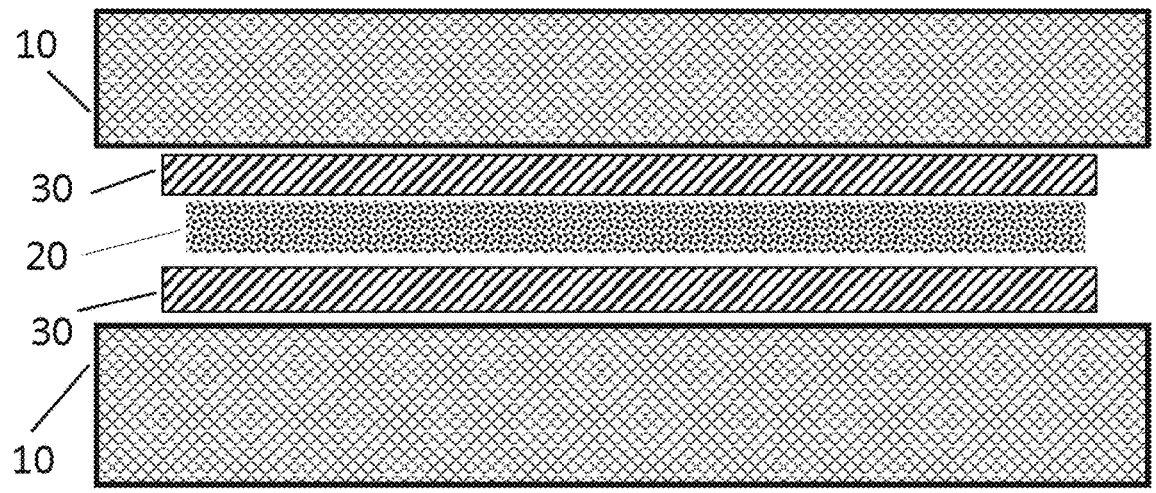
Figure 16:
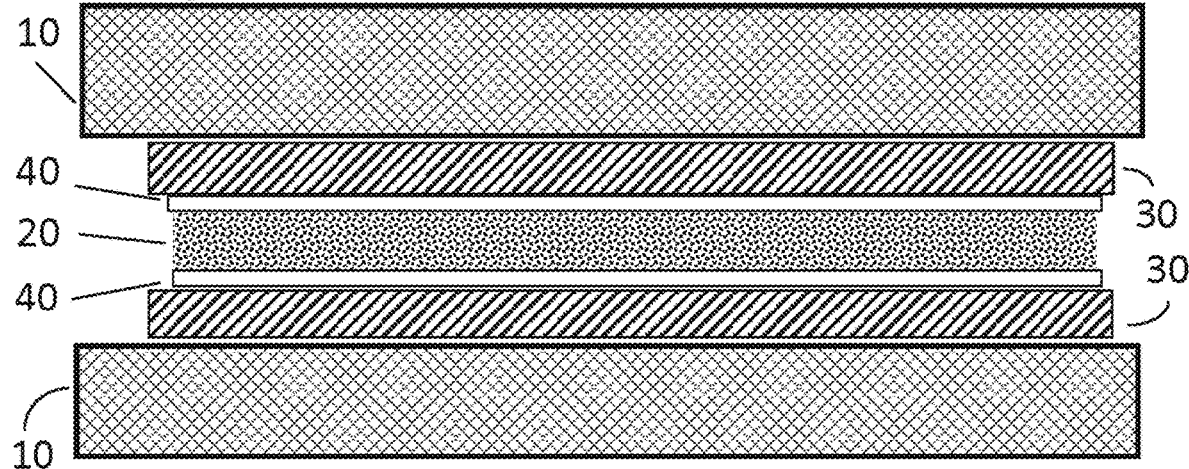

We chose to incorporate a folded metal film carrier for the pulverized material to simplify the material handling. In this way a portion of a heat conducting film or foil, such as aluminum foil 30, has the powdered material 20 evenly distributed in a thin layer on portion of foil. This is covered with another similar layer of foil. The edges may or may not be folded over. When folded over at the four edges, by typically ⅛-³⁄₁₆" at each edge a sealed, flat package is formed which is easily maneuverable for heating, while minimally disturbing the thin layer of material inside To minimize adhesion of melted resin to the foil or plates the plant material may first be enclosed within a folded parchment sheet 40. This is either wrapped in foil or placed directly between the plates. FIG. 16C.

Heating Methods

Decarboxylation reports using ovens may not use precision ovens. Conventional ovens set for a certain temperature, say 325° F. (162° C.) can easily fluctuate 25° above or below the set temperature due to thermostatic heating. Over enough cycles of these fluctuations the temperature should average out to the setpoint. Over short time intervals as those used in thin layer decarboxylation such fluctuation is contrary to precise temperature control.

As a first approximation two flat heat retaining objects are preheated in a conventional oven at a preset temperature. The objects are not in contact as they preheat. The temperature of the surfaces are monitored with a remote hand held infrared thermometer until they stabilize near the preset temperature. The temperature fluctuation of the surfaces is much slower than the oven and begins to approach more precise temperature control.

In its most basic embodiment the dried *cannabis* plant matter sprinkled in a thin layer on one surface, quickly leveled, then the second heated surface placed on top of the thin layer, FIG. 16a. The matter is held between the plates for a specified time. The time is determined by calibrations of the specific apparatus being used. When the time expires the plates are separated and the decarboxylated *cannabis* is transferred to a suitable collecting vessel. The collecting vessel is preferably immediately placed on ice in a freezer until cooled.

Depending on the heating surfaces the decarboxylated *cannabis* may tend to stick to the heating surface when removal is attempted. This is due to the melted resins congealing. Those that persist at the surface will tend to adhere the *cannabis* to the heating surface. With repeated cycles of use the residue buildup could become significant and cause undesired buildup. Repeated heating of such a residue could cause degradation followed by contamination of fresh samples coming through.

An alternative embodiment contains the thin layer of *cannabis* between two layers of metallic foil, FIG. 16b. The foil permits ease of handling of the thin layer. Further it allows maximal heat transfer to the thin layer. A piece of foil approximately 6"×8" is folded in half to a 6"×4" size. The top half is opened exposing the bottom layer of foil. The thin layer of dried, pulverized *cannabis* is sprinkled on the bottom half of the foil, then leveled. The upper half of the foil is folded down to cover the thin layer. This foil packet can be placed directly into the preferred decarboxylation arrangement.

The folded foil containing the thin layer can be further stabilized by folding the edges over. Approximately ¼ inch of the double layered edge of the foil container is folded over across the top of the packet. This is continued with the other two unsealed edges of the foil. The folding partially seals the contents from the atmosphere. It also thickens the edge providing more rigidity and reinforcement. This greatly facilitates handling of the thin layer, while minimizing disruption of the thin layer.

With some particularly resinous cultivars the sticking may continue to be a problem. This is mitigated by placing the thin layer between two layers of parchment paper or its equivalent. The enclosed thin layer is placed directly between the heating surfaces. Alternately the parchment packet can be enclosed in an edge reinforced foil packet as above, FIG. 16 C.

Figure 17:
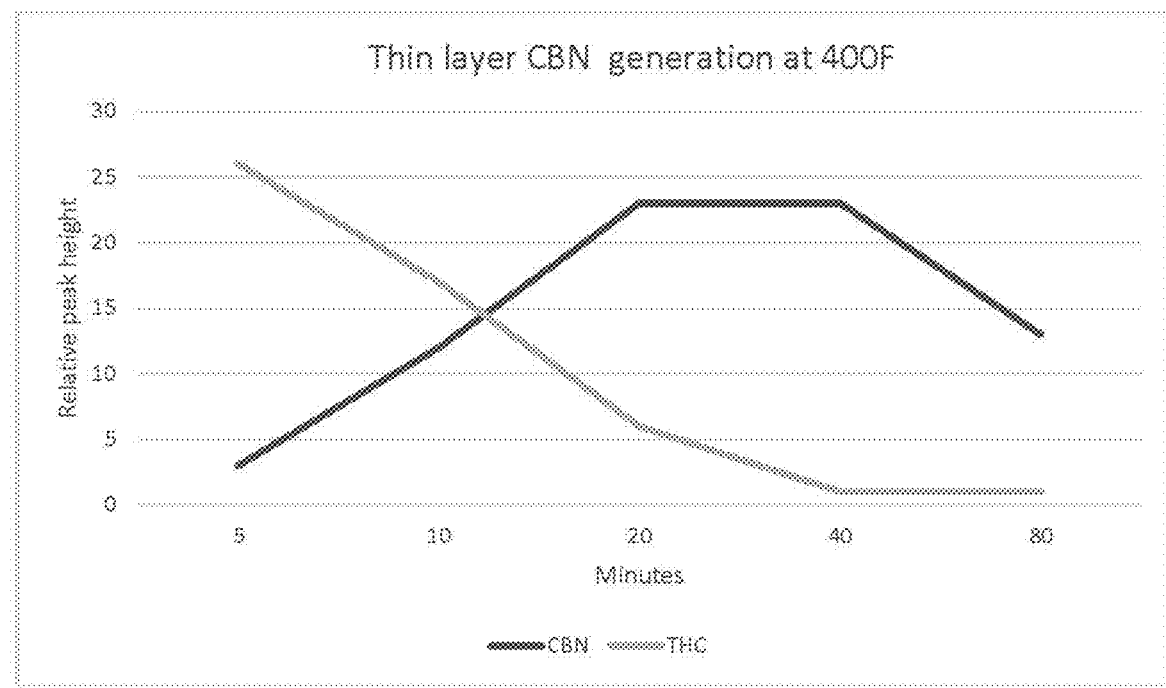
FIG. 17 shows CBN generation using the thin layer method

CBN production is seen in FIG. 17. It is remarkably absent under most thin layer decarboxylations. At 400 deg F. both THCA and CBDA are fully converted in under a minute. If the heating continues to 5 min CBD formation is noted to begin, While THC levels are decreasing. The CBD peaks at 20 min and begins to decay at 40 min when THC has declined to zero.

Another embodiment uses heat sealable metallized bags, such as mylar. A 6×8" piece of parchment paper is folded into a 6×4" packet as above. A 1 gallon mylar bag is trimmed to fit between the heating surfaces with no overhang along the edges, such that when the surfaces are closed and contacting the packet, the entire packet is contained against a heating surface. The thin layer is placed on one half of the parchment packet and the other half folded over the top. Without lifting the parchment packet from its supporting surface it is slid into and against the bottom seam of the mylar bag. Or as much as possible the parchment packet is stabilized and the mylar bag is slid onto the parchment packet. The opened edge of the mylar bag is left unsealed.

The loaded mylar bag is placed between two heating surfaces. It is allowed to heat for the prescribed time. Immediately and for several seconds any retained water in the *cannabis* turns into steam and out gases from the *cannabis*. If the bag is sealed and there is sufficient *cannabis* and retained water in the thin layer the expanding steam can be sufficient to cause explosive rupture of the sealed bag. Therefore it is imperative the open mouth of the mylar bag is not sealed before placing between the heated plates!

The temperature used for the mylar bag decarboxylation is 300° F. (150° C.). At this temperature the polyethylene lining of the mylar bag slowly melts over the first 30 seconds or so. Thus the mouth is initially open and generated steam vents through the opening, despite it being only a narrow slit, until the steam is exhausted. The polyethylene lining remains plastic in the heat and the edges of the open mouth of the bag fuse. When the flattened bag is removed from the plates it is preferably immediately transferred onto ice in a freezer. The rapid cooling causes the fused edges of the polyethylene to harden, sealing the bag.

The bag self seals as soon as it is removed from the plates. There's no further ingress or egress of gases. As cooling progresses any trapped gases which had increased their volume due to heating will decrease their volume with cooling. The decreased volume of the gases results in a decrease in pressure and a vacuum effect, collapsing the bag onto the contents. This provides a hermetically sealed vacuum packed thin layer of decarboxylated *cannabis*. These packages are conveniently stored at ambient or freezing temperatures for prolonged storage.

An embodiment of the opposed heated plates captures the steam terpene mix. One or more ports are drilled through the bottom heating plate of the Panini press, somewhere in the perimeter outside of the space where the thin layer packet will sit. The perimeter of the heating plates are adapted to provide a vacuum/pressure seal when closed. The outgassing of steam and terpenes will be through the port, directed to a condenser and collected.

An alternative embodiment to heat the thin layer is a premade mechanism such as a Panini press with flat plates and sufficient motion to approximate the two plates. (1000 want IMUSA Panini press). FIGS. 18a and 18b. As constructed this press uses thermostatic temperature control similar to ovens discussed above. Similarly a 50° temperature swing was observed under thermostatic control. The thermostat was bypassed eliminating any internal temperature control of the press. It was then plugged into an external controller (Auburn PID controller), FIG. 19. The controller parameters were set by auto tuning the controller at each temperature used. This provided temperature control within a few degrees.

Simple Methods for Personal Use are Readily Available

Another embodiment, amenable to large-scale production requires two flat (at the point of contact), opposable, heatable surfaces such as ceramic or metal plates, rollers, opposable conveyer belts, tank tread conveyor or others.

Cooling

The thin layer or foil packet is heated for the prescribed time, then within one two seconds placed on ice in a freezer, reducing the temperature to freezing within seconds.

Heating

Two flat opposable surfaces preferably both of heatable material, with precisely controllable temperature and of sufficient reserve heat to maintain a constant temperature while rapidly heat a thin layer of pulverized material when contacted on one or both sides of the thin layer of material by the heat sink surfaces, trapping the thin layer into direct contact with the heated surface(s),

THC

To date most work has been done with the conversion of THCA to THC. It has been done preceeding extraction, or to further process into edibles, this step is necessary to activate the psycho activity of the THC. When being smoked or vaporized the THCA is converted by the heating or vaporization, though it is reported this is incomplete since significant amount of THCA remains in the smoke or vapor.

CBD

More recently interest has been greatly increased in the non-intoxicating compound CBD. It is similarly decarboxylated prior to extraction. As techniques improve in analyzing, and breeding for specific cannabinoids, which will exist in their acidic form while in the plant and amenable to decarboxylation, it will allow using previously commonly unavailable cannabinoids in to be used in formulations.

Ingestion

The decarboxylated material is cooled and distributed in bulk or further processed into dosing units. The material is also made available for single dose ingestion in the form of powder, tablets or capsules.

The powder can be eaten directly, or placed in any edible or drink. There is no need for further cooking, and the material does not need to be soluble as it is already ingestible by simply swallowing the activated material. It is readily assimilated when added to virtually any food or drink. The material also retains its potency for smoking if desired.

Principle Acidic/Neutral Pairs

With continued breeding successes of appropriate cultivars it is expected the major acidic/neutral pairs will become available including all of the propyl and pentyl cannabinoids, including:

| Pentyl | Propyl |
| --- | --- |
| THCA/THC | THCVA/THCV |
| CBDA/CBD | CBDVA/CBDV |
| CBGA/CBG | CBGVA/CBGV |
| CBCA/CBC | CBCVA/CBCV |

And Others:
CBNA/CBN,
CBCA/CBLA
CBLA/CBL
CBL/CBL
And Delta 8THC
Oven Method
Stone/Pan Two surfaces can be produced using commonly available materials, for example a ceramic plate of the type used for baking pizza and a flat bottomed cast iron pan. The surfaces are preheated in an oven to the desired temperature. Surface temperatures are measured with a hand held infrared thermometer. A packaged thin layer is placed on the ceramic plate, the cast iron pan is placed on top of the packet. After the desired decarboxylation time the packet is rapidly removed and chilled as above.

Homogenization

Homogenized plant material was prepared to maintain a uniform consistency and chemical uniformity. For analysis of each sample two hundred mg aliquots of the homogenized plant material were sprinkled in a fine layer onto a thin piece of metal foil, which was folded over, enclosing the sample in a flat thin manner.

Panini Press

A second method is easily achieved using a small panini press. Temperature control is achieved with a PID controller. Conventional heating devices use thermostatic control allowing temperature swings of 25-50 deg F. depending on the set temperature. With such an unpredictable heating the decarboxylation is less predictable and a significant change in the conversion, which if incomplete could mean potential waste of material.

The sample was placed between flat metal plates preheated to the working temperature. The temperature was monitored and maintained to within one degree via a PID controller. Heating apparatus used was a commercial 1000 W panini press with flat plates. The PID controller was an Auburn Instruments WSD-1501GPH, FIG. 19.

Alternative Configurations

Further methods could be employed for individual use with a variety of existing products. For example an electric cooking grill, an iron, electric frypan and others. Those skilled in the art will certainly envision use of alternative methods. The two-sided heating is most effective and predictable and how our data was obtained. It is of course possibly done using a single heated surface and an opposed nonheated surface applied with enough pressure to ensure sufficient contact to the heated surface. If the heat is sufficiently high enough and constant on one side of the thin layer, and the layer thin enough, with enough heat penetration possibly a less efficient conversion could be achieved.

Commercial/Automated

To use the method on a commercial scale the same principles are applied, namely a thin layer of material caught in contact between two heated flat surfaces, (or a nonheated flat surface pressing the material sufficiently to contact a heated flat surface). Automated methods would be preferable. Precise temperature control is desirable in all embodiments for the predictive conversion values to be accurate and to minimize waste.

Conveyor

Another method is a horizontal conveyor with either heated belts 104 and 106 or rollers 108 in an oven to maintain the working temperature. The upper conveyor belt 104 is positioned so its flat surface runs opposed and in contact with the lower conveyor belt 106. Again, the heat may be in either or both heated contact surfaces, preferably both. A hopper 102 over the bottom belt 106 forms the thin layer 20 as a feeder dispenses as the belt 106 moves beneath it at a constant speed, FIG. 10.

To use the automated conveyor the temperatures of the heated conveyor 104 and 106 and chilled conveyor 112 are stabilized. The hopper 102 is filled with pulverized *cannabis* plant material. Based on the heat of the conveyor the selected time for the decarboxylation is chosen. The speed of the conveyor belt 104 and 106 is then chosen so the transit time through the heating part of the conveyor belt matches the decarboxylation time. The hopper 102 dispenses the pulverized *cannabis* in a linear fashion across the width of the lower conveyor belt 106. The output of the hopper 102 is such that as the conveyor 106 passes underneath the curtain of *cannabis* matter falling from the hopper is essentially laid onto the conveyor in a thin layer 20. The thickness of the layer is a function of the dispensing rate and the speed of the conveyor 104 and 106.

The thin layer 20 is carried on the conveyor 104 and 106 through the heating portion to decarboxylate to the desired degree based on the time and temperature determinations. (At the end of the heated conveyor the lower belt is routed downwards and around its loop back to the hopper 102. The upper loop is routed upwards and around back to the beginning of the heating segment.) As the belt's turn at the end of the heating segment the exiting thin layer 20 falls onto a tilted plate, the scraper 110 which directs the thin layer onto the chilled conveyor belt 112. The edge of the scrapers 110 ride gently on the surface of the upper 104 and lower 116 conveyor belts immediately above and below the exiting thin layer 20 to clean the belts of the decarboxylated *cannabis* and direct it to immediate cooling.

The thin layer is rapidly cooled on the chilled conveyor 112. As it reaches the end of the conveyor the resins in the thin layer will have solidified and frozen, losing their stickiness, and falling into a collector 122.

Another method is to have the opposed surfaces instead of belts be a looped series of serially chained heated plates FIG. 11. With two opposing loops, two opposing plates would meet and contact as a thin layer 20 is inserted between the plates 200

The conveyor continues for the predetermined time and speed until the hinged plates separate at the exit of the heating stage and the decarboxylated thin layer 20 is free to fall. The wafer falls onto a sloped receiving service which directs it to the chilled conveyor belt.

Alternately instead of applying the *cannabis* directly to the hinged plate conveyor belt appropriately sized parchment/foil or mylar bag containing thin layers can be applied to the conveyor belt for decarboxylation. Similarly the transit time determines the heating time. On exiting the opposed hinged plate conveyor belt the packet falls freely is caught by a receiving plate and directed to the chilled conveyor as before.

Looped Hinged Plates (Panini Presses)

Another configuration would be a series of heated flat hinged plates like panini presses. FIG. 12. These can be linked to travel along a horizontal loop, the looping time controlled for the decarboxylation or chemical conversion. As the system indexes in a circle, stationary positions adjacent to the moving hinged plate units would be controlled to insert a thin layer as prefolded packets or material, removing the packets or material at another station. Again immediate chilling of the product is desirable.

The hinged plates are first allowed to equilibrate to temperature. At station 1 hinged plates 302 are open and packet containing thin layer is inserted. The upper half of the hinged plates is closed. The group of hinged plates 308 are indexed one step, in this case counter clockwise. The timing is such that the transit time for a thin layer inserted in station one to its removal at Station zero is that required to progress the decarboxylation to its desired completeness. In this example with a clamshells the time spent at each station plus the time required to change stations would be equal to the total time divided by eight, giving a time interval. This time interval is the indexing interval. The time spent in decarboxylation is seven indexing intervals since the sample is removed at station 0 and inserted at station 1.

The loading and unloading of the hinged plates can also be automated. At station one a dispenser of stacked thin layer packets pushes a packet into the open hinged plates. Completing the cycle as the hinged plates opens at station 0 a retrieval means such as a rod contacts the packet, pulls it out, dropping it into a freezing chamber.

An alternative embodiment to the rotating hinged plates group is a stationary linear array of hinged plates with a movable dispensing and retrieving unit. It's transit time to address one cycle of the array equals the total decarboxylation time. The linear actuator positions the movable dispensing/retrieving unit adjacent to the appropriate hinged plate station. The hinged plate is opened by an actuator. The packet completing its decarboxylation is retrieved and dropped into the freezing compartment in the mobile dispensing/retrieving unit. The dispensing unit slides a packet into the open hinged plates. The actuator closes the hinged plates. The dispensing/removing unit indexes to the next hinged plates in the sequence, effected by the linear actuator. If the packet used is the resealable mylar bag the units are ready for dispensing, for storage, or as is or proceed to further formulation.

Print Dryer Configuration

A single side heated apparatus is easily made similar to a photographic print dryer. FIG. 13. A large heated drum 402 is slowly rotate about its axis and a continuous belt 400 contacts it following the drum surface 404. If a thin layer 20 of *cannabis* is allowed on the belt 400 then the belt 400 holds the thin layer in contact to the heated drum and following it, the duration of contact predetermined from known data, the conversion is accomplished. As the thin layer 20 comes off the drum surface 404 and is transported away it is preferably immediately chilled as above. The belt 400 can contain an integral electrical coil or other heating means to have a heated belt. This allows two-sided heating, a more effective, faster and predictable method. The belt should also be gas impermeable to minimize loss of compound to vaporization and escape from the system.

To use the revolving drum reactor, it is first allowed to heat up to decarboxylation temperature and reach thermal equilibrium. The decarboxylation time is related to the temperature. From previous calibration curves the time is selected for the given temperature, based on the degree of decarboxylation desired. As the heated drum 402 revolves it engages the belt 400 against its surface. The rollers 408 are adjusted to maintain appropriate tension on the belt.

The hopper 102 provides a trickle feed of pulverized *cannabis* matter in a linear fashion across the moving belt 400. At the consistent speed of the feed and the belt the uniform thin layer is produced on the belt 400. The drum 402 continues to turn and the belt advances in unison, engaging the thin layer 20 between the belt 400 and heated drum surface 402. The time to rotate through one cycle of the drum 402 is fixed to the decarboxylation time. In this case the decarboxylation parameters will likely require a slightly higher temperature and or longer decarboxylation time due to the majority of heating by the drum 402 is on a single side of the thin layer only. A belt 400 with reflective properties would help maintain the temperature. The belt being gas tight prevents exposure to the atmosphere during decarboxylation. It does not prevent escape of the steam and terpenes. The belt 400 can be heated also providing dual sided heat to the thin layer 20.

The entrapped thin layer 20 completes its transit around the drum 402 until the belt 402 is pulled away from the drum 402 by the positioning of roller 408. As the belt 400 is pulled away the decarboxylated *cannabis* is free to fall and be directed to a receiving vessel 418. At this point on the drum 402 a scraper 406 is placed laterally in contact and across the surface of the drum. As some of the decarboxylated *cannabis* sticks to the surface of the drum 402 the scraper 406 cleans it off as the drum 402 rotates. The scraper 406 then collects the loose decarboxylated *cannabis* and directs it towards a receiving trough 414 which further directs it to a receiving vessel 418 preferably within a freezing environment.

Multiple Acidic/Neutral Pairs

In the event a material contains more than one compound of interest, in this case THC and CBD, the optimal simultaneous conversion or decarboxylation times to maintain maximum conversion without a low yield or degradation to occur of either compound is predictable by the presented data. The data points represent the time to peak concentration of THC or CBD and corresponding disappearance of THCA and CBDA. As such, in a sample with significant THC and CBD the optimal heating would continue until peak CBD level while maintaining peak THC level. These THC levels are found to remain constant without conversion to CBN until after the CBD level peaked.

CBN Production

CBN appears at much longer heating times. At 400 F CBN appears at 320 sec, when THC is down to 50% of its peak. CBN reaches its maximum at 20 min. when there is only a trace of THC remaining, FIG. 17. Standards for CBN were unavailable but the identity could be inferred due to the concurrent, inverse evolution to the THC disappearance. Further the appearing compound showed absorption at 290 nm, whereas the other compounds do not Dosing

TABLE 1

| Pharmacologic Actions of cannabidiol |
| --- |
| Examples of actions induced by CBD at <1 uM |
| Decreased |
| Effects induced by CB1/CB2 receptor agonists |
| Cytochrome P450 enzyme activity |
| Increased |
| Membrane fluidity |
| Examples of actions induced by CBD at 1-10 uM |
| Decreased |
| Activation of alpha1 adrenoreceptors and u-opioid receptors |
| Cellular uptake of anandamide |
| Synaptosomal uptake of noradrenaline, dopamine, 5-HT and gamma butyric acid |
| Cancer cell proliferation |
| Human keratinocyte proliferation |
| Oxidative stress |
| Lipoxygenase activity |
| Phospholipase A2 activity |
| Increased or activated |
| TRPV1 receptor |
| Signs of neuroprotection |
| Membrane stability |
| Examples of actions induced by CBD at >10 uM |
| Decreased |

TABLE 1-continued

| Pharmacologic Actions of cannabidiol |
| --- |
| Cellular uptake and metabolism of anandamide |
| Cyclooxygenase activity |
| Allosteric modulation of mu and delta opioid receptors |
| Ativated |
| 5HT-1a receptor |

The dosing of CBD for a given range of activity is predictable, Table 1. In the summary of pharmacological actions of CBD, FIG. 1, desirable activity such as decreased oxidative stress, antiproliferative activity, neural protection and anti-inflammatory effects are reported between concentrations of 1-10 micromolar. This is a desirable group of activities to select. CBD at one micromolar is equivalent to 0.3 ng per ML and 10 micromolar is equivalent to 3 ng per ML. AUC for CBD ranges widely for different subjects but reportedly averages about 4 ng hour per ML. A single dose of 4 mg would provide an average 0.16 ng/ml concentration over 24 hours. An 8 milligrams dose would provide an average of 0.32 ng per ML over 24 hours, about one micromolar. Thus in 80 mg dose would provide an average of 10 micromolar over 24 hours. A single dose would produce a single large peak with return to baseline within about 10 hours, again this is variable between individuals. It is known that as frequency of dosing increases the plasma concentration will approach a steady-state or constant value between doses, eliminating the large peaks and valleys associated with infrequent doses. A reasonable dosing schedule might be 25 mg CBD three times daily to achieve 75 mg daily, about 9.4 micromolar average, at the high end of the 1-10 uM range. Similarly a 2.5 mg dose every eight hours would yield an approximately 1 micromolar average concentration.

EXAMPLES

Formulating Prescription

Figure 20:
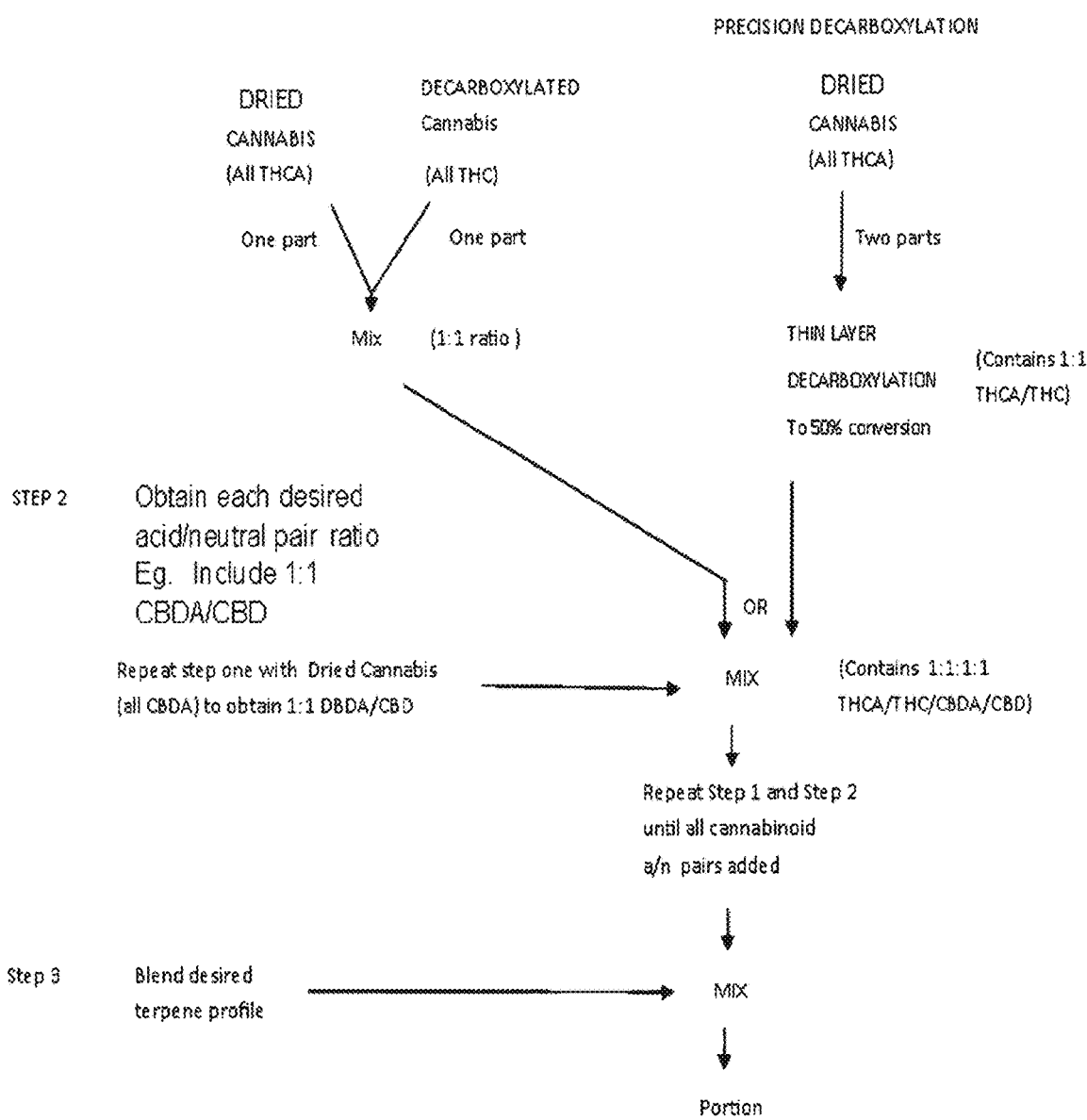
FIG. 20 shows the map of the method for using decarboxylated *cannabis*

FIG. 20. shows the map for the method of using decarboxylated *cannabis*.

Step 1—Obtain ratio for a single acidic/neutral pair

Option 1 Blend raw and fully decarboxylated *cannabis*.

Since raw, dried *cannabis* contains virtually no THC but exists as THCA and completely decarboxylated *cannabis* contains 100% THC, no THCA, a 1:1 mixture of raw and completely decarboxylated quantities of the same *cannabis*, provides a 1:1 mixture of THCA:THC.

Option 2 Precision decarboxylation

A 1:1 ratio of THCA:THC is obtained by heating in a thin layer for the time determined by the calibration curve of a given apparatus at the point where the THCA and THC curves intersect, ie the equimolar point.

Step 2 If another ratioed pair is desired, repeat Step 1 with the appropriate *cannabis* containing the acidic component of the pair. Repeat as necessary, then blend ratioed cannabinoid pairs to obtain appropriate weight ratios.

Step 3 Blend and apply terpenes

Step 4 portion as needed

A dispensary will provide the total cannabinoids content as a percentage, a total of the percentages of the neutral and acidic forms, for example THCA+THC. After decarboxylation the content of cannabinoid is completely in its neutral form and the amount is predictable knowing the initial percentages. For example 18% THCA+0.5% THC is commonly reported as 18.5% THC.

Note: this is common and overestimates the total cannabinoid content. In actuality about 12% of THCA is lost in the process of decarboxylation as the carboxyl moiety is liberated. Therefore the total estimated THC, assuming 100% conversion, is (0.88×THCA+THC). Technically this can further be corrected as sometimes the conversion may not be complete. This would depend on the specific methodology.

"Dried" refers to the as dispensed *cannabis*, non-decarboxylated and including water weight residual from the curing and drying process.

In the above example 18% THCA in the "dried" *cannabis* as dispensed would be 180 mg THCA/g "dried".

Expecting a 12% decarboxylation loss means

180×0.88=158.4 mg THC equivalent from THCA/g "dried"

expecting a 15% average water loss 158.4/0.85 g "dried" after decarboxylation water loss=

186 mg THC/g decarboxylated, contributed by THCA from original gram "dried"

Adding THC from original "dried"

186+0.05×180=186.9 total THC/g decarb, ie 18.7%.

Therefore corrections for water loss and CO2 loss of decarboxylation cancel each other when the "dried" *cannabis* water content is 10-15%.

Example THCA/THC 1 to 1 Ratio

For example to achieve a 1:1 ratio of THCA/THC with the 10% assayed material, equal amounts by weight of the dried *cannabis* (all THCA) with the decarboxylated *cannabis* (all THC) is blended. Now the final product would contain 5% each of THCA and THC, or 5 mg THCA and 5 mg THC per gram of CC.

Example THCA/THC 1 to 1 Ratio

For example to achieve a 1:1 ratio of THCA/THC with the 10% assayed material, equal amounts by weight of the "dried" *cannabis* (all THCA) with the decarboxylated *cannabis* (all THC) is blended. Now the final product would contain 5% each of THCA and THC, or 5 mg THCA and 5 mg THC per gram of CC.

Note: these calculations use gross weight by percentage, i.e. milligram to milligrams. The most precise calculation for accuracy in prediction of the final product would be done stoichiometrically, as the number of moles substrate will become the same number of moles product.

Example CBGA:CBCA:CBDA:THCA in a 1:1:1:1 Ratio

In another example, cancer, it has been shown the combination of penta-cannabinoid acids is more effective than them individually. In other words a prescription calling for CBGA:CBCA:CBDA:THCA in a 1:1:1:1 ratio is easily achieved by mixing the dry *cannabis* of the four types in plants unique for them, meaning containing a single major cannabinoid, and in their acidic forms as the material would not have been heated. The four different types of *cannabis* are then blended in cannabinoid weight equivalent volumes to reach the ratio.

For example 4 types of dried *cannabis* containing:

| CBGA 6% |
| CBCA 3% |
| CBDA 9% |
| THCA 10% |

Each of these is diluted by 4 after blending.
The maximum concentration attainable will be limited by the most dilute component.

| Start CBCA 3% 1 g equals 30 mg CBCA |
| CBGA 6% 1 g equals 60 mg CBGA |
| CBDA 9% 1 g equals 90 mg CBDA |
| THCA 10% 1 g equals 100 mg THC |

Blending for each gram of CBCA, 0.5 g CBGA (30 mg), with 0.33 g CBDA (30 mg) with 0.3 g THCA (30 mg) will total 2.13 g containing 30 mg of each of the 4 acidic cannabinoids, yielding 14 mg/g of each cannabinoid or 1.4 mg each per 100 mg dose.

Example CBDA/CBD/THCA/THC in a 1:1:1:1 Using Precision Decarboxylation

Using the controlled decarboxylation method to achieve a 1:1:1:1 ratio of CBDA/CBD/THCA/THC. Firstly a strain of THC only *cannabis* of a known total concentration is heated in a decarboxylator for the time as mentioned above where the plotted molar concentration lines cross. The *cannabis* will now contain a 50-50 or a one-to-one ratio. Similarly a CBD only strain is half decarboxylated. If the CBD strain and THC strain were both 10%, then equal amounts of each 50-50 mixture will provide the 1:1:1:1 mixture. If the CBD and THC strains were different concentrations they would be proportioned as above to equal molar amounts in this case.

Similarly other mixtures of acidic and/or neutral cannabinoids are made with dried or decarboxylated *cannabis*.

Terpene Addition

A mixture of terpenes can be supplemented into the cannabinoid containing mixture to provide synergistic benefits toward a desired formulation. As the cannabinoid mixture is geared toward a suitable indication, in a synergistic manner, the terpene selection is similarly done to optimize synergistic actions.

A typical supplementary mix of terpenes would total 10% or less of the total weight of the custom *cannabis*.

To prepare the terpene mixture, aliquots of a terpene in its pure form are blended to contain the desired percentages of each terpene. Then the desired weight of the terpene mixture, up to 10% of the weight of the custom *cannabis* is applied to the cannabinoid containing custom *cannabis*. Terpenes are applied in a liquid form as a spray or drops in an amount equal to 10% total weight. The mixture is then briefly homogenized to distribute the terpenes uniformly.

For antidepressant actions cannabinoids are selected from the group containing CBG and terpenes are selected from the group containing beta caryophyllene, limonene, linalool, myrcene, phellanderene.

For anti-insomnia actions cannabinoids are selected from the group containing THC and terpenes are selected from the group containing beta caryophyllene, Borneol, pinene.

For relaxant actions terpenes are selected from the group containing borneol, and phytol.

For sedative actions cannabinoids are selected from the group containing CBD and CBN and terpenes are selected from the group containing borneol, carene, linalool, myrcene, nerodilol, terpineol, and terpinolene.

For anti-anxiety actions cannabinoids are selected from the group containing CBD and terpenes are selected from the group containing beta caryophyllene, borneol, linalool, and terpinolene.

For analgesic actions cannabinoids are selected from the group containing THC, CBN, CBG, CBCA and terpenes are selected from the group containing beta caryophyllene, bisabolol, borneol, eucalyptol, linalool, menthol, sabinene, and terpinolene.

For anti-inflammatory actions cannabinoids are chosen from the group containing CBD, CBGA, 9 THC, 9 THCA, CBN, and CBC and terpenes are chosen from the group containing beta caryophyllene, bisabolol, borneol, camphene, carene, cymene, eucalyptol, guaiol, humulene, isopulegol, menthol (topical), myrcene, pinene, terpinolene, and valencene.

For antioxidant actions cannabinoids are chosen from the group containing CBD and THC and terpenes are selected from the group containing beta caryophyllene, bisabolol, camphene, fenchol, geraniol, myrcene, nerodilol, terpineol, and terpinolene.

For antibacterial actions cannabinoids are chosen from the group containing CBD, CBDA, CBG, CBN and CBC and terpenes are chosen from the group containing bisabolol, camphene, camphor, cedrene, cymene, eucalyptol, fenchol, geraniol, guaiol, humulene, isopulegol, myrcene, nerodilol, ocimene, and terpineol.

For antifungal actions cannabinoids are selected from the group CBD, THC, CBG, and CBC and terpenes are selected from the group containing biabolol, carene, caryophyllene oxide, cedrene, eucalyptol, geraniol, myrcene, nerodilol, and ocimene.

For anticancer activity cannabinoids are chosen from the group containing CBD, CBDA, 9 THC, CBGA, and CBG and terpenes are selected from the group containing beta caryophyllene, bisabolol, cedrene, humulene, limonene, myrcene, phellanderene, and phytol.

For antispasmodic activity cannabinoids are chosen from the group containing CBD, 9 THCA and THC and terpenes are selected from the group containing beta caryophyllene, and myrcene.

For anticonvulsant activity cannabinoids are chosen from the group containing CBD, CBN and THCV and terpenes are selected from the group containing beta caryophyllene, geraniol, isopulegol, and linalool.

For bronchodilator activity cannabinoids are chosen from the group containing THC and terpenes are chosen from the group containing borneol, eucalyptol, and pinene.

for anti-coagulant activity terpenes are chosen from the group containing borneol, and caryophyllene oxide.

For neuroprotective activity cannabinoids are chosen from the group containing CBD, THCA, THC, CBN and as a memory aid terpenes are chosen from the group containing carene, pulegone, pinene, and terpineol.

For antimalarial activity terpenes are chosen from the group containing nerodilol, and terpineol.

For gastric cytoprotective activity cannabinoids are chosen from the group containing THC and terpenes are selected from the group containing beta caryophyllene.

For wound healing activity terpenes are selected from the group containing bisabolol.

For cough suppressant activity terpenes are chosen from the group containing borneol.

For decongestant activity terpenes are selected from the group containing camphor.

For antiplatelet activity terpenes are chosen from the group containing caryophyllene oxide.

For local anesthetic activity terpenes are chosen from a group containing beta caryophyllene, and borneol.

For AEA uptake inhibitor activity cannabinoids are chosen from the group containing CBG and CBC.

For anorectic activity cannabinoids are chosen from the group containing 9 THCV.

For antidiabetic activity cannabinoids are chosen from the group containing CBD.

For anti-emetic activity cannabinoids are chosen from the group containing CBD, CBDA, 9 THCA, 9 THC, and CBDV.

For anti-erythema activity cannabinoids are chosen from the group containing CBG.

For anti-ischemic activity cannabinoids are chosen from the group containing CBD.

For antipruritic activity cannabinoids are chosen from the group containing 9 THC.

For anti-psoriatic activity cannabinoids are chosen from the group containing CBD, CBN and CBG For antipsychotic activity cannabinoids are chosen from the group containing CBD.

For antiviral activity cannabinoids are chosen from the group containing CBC.

For appetite stimulant activity cannabinoids are chosen from the group containing 9 THC, 8 THC and CBN.

For bone stimulant activity cannabinoids are chosen from the group containing CBD, CBG, CBC, 9 THCV, CBDV and CBN.

Four immunosuppressive activity cannabinoids are chosen from the group containing CBD.

For intestinal anti-Pro kinetic activity cannabinoids are chosen from the group containing CBD.

For decreased intraocular pressure activity cannabinoids are chosen from the group containing 9 THC, CBN and CBG.

For LOX blocker activity cannabinoids are chosen from the group containing CBD and CBG.

For mood stabilizer activity cannabinoids are chosen from the group containing CBG.

For psychoactive activity cannabinoids are chosen from the group 9 THC and CBN.

For anti-sleep apnea activity cannabinoids are chosen from the group containing 9 THC.

For vasorelaxant activity cannabinoids chosen from the group containing CBD.

For anti-overdose activity of THC, cannabinoids are selected from the group containing CBD and terpenes are selected from the group containing beta caryophyllene, limonene and pinene.

Dosing

Inhaled forms are felt immediately, sublingual or sprays take about 20 minutes to be felt and swallowed medicine take 45 minutes or longer to be felt.

When taking THC orally especially in repeating doses the slow sustained buildup can result in over medication and toxic side effects.

Sublingually dosing allows for faster onset.

THC and CBD follow a bell shaped dose response curve for some activities, meaning low dose, little effect, medium dose maximal effect, high-dose little effect. The maximal effect range is sometimes referred to as the "sweet spot".

Prescription

*Cannabis* is typically not dispensed by prescription at this time. Generalized recommendations are made regarding THC and CBD content by weight and ratios to each other.

As more knowledge is gained and new cultivars expressing previously unavailable cannabinoids advance more useful compounds will become available. To develop cultivars with specific cannabinoid profiles as well as terpene profiles for specific activity will be an extremely time consuming process. Once developed these cultivars will mostly have a single use. Therefore a system to make available useful cannabinoids and terpenes in a precise, reproducible and rapid fashion is highly desirable.

We will describe such a method for prescriptive *cannabis* with the presumption that all the possibly available cannabinoids are indeed available.

A therapeutic prescription would include providing the ratios and the relative weights of the prescribed cannabinoids, most typically the major and propyl cannabinoids but also precursors, metabolites and derivatives.

This includes

| | | |
|---|---|---|
| THCA/THC | THCVA/THCV | Delta 8 THC |
| CBDA/CBD | CBDVA/CBDV | CBNA/CBN |
| CBCA/CBC | CBCVA/CBCV | CBCA/CBLA |
| CBGA/CBG | CBGVA/CBG, | CBCA/CBL |
| | | CBLA/CBL. |

Is highly desirable to include terpenes in a formulation for their synergistic activity with the cannabinoids, also called the entourage effect. The most common terpenes seen in *cannabis* include:

| | | | |
|---|---|---|---|
| beta caryophylline | cedrene | isoborneol | phellandrene |
| bisabolol | cymene | isopulegol | phytol |
| borneol | eucalyptol | limonene | pulegone |
| camphene | fenchol | linalool | pinene |
| camphor | geraniol | menthol | sabinene |
| carene | geranyl acetate | myrcene | terpineol |
| caryophyllene oxide | guaiol | nerolidol | terpinolene |
| | humulene | ocimene | valencene |

Alternately, rather than prescribing individual terpenes the prescription may select terpenes based on their activities. The selection may appear as follows:

| | | | |
|---|---|---|---|
| AEA uptake inhibitor | anti-ischemic | bone stimulant | local anesthetic |
| anorectic | Antimalarial | Bronchodilator | LOX blocker |
| Antibacterial | Antioxidant | cough suppressant | memory aid |
| Anticancer | Antiplatelet | Decongestant | mood stabilizer |
| Anticoagulant | antipruritic | decreased intraocular pressure | muscle spasm |
| Antidepressant | anti-psoriatic | Epilepsy | Pain |
| antidiabetic | antipsychotic | gastric cytoprotective | psychoactive |
| anti-emetic | anti-sleep apnea | GI. | Relaxant |
| anti-erythema | antiviral | immunosuppressive | Sedative |
| Antifungal | Anxiety | insomnia | vasorelaxant |
| anti-inflammatory | appetite stimulant | intestinal anti-Pro kinetic | wound healing |

If a prescription becomes complex patients will rely on accessible dispensaries. Once a producer knows the cannabinoid content of a specific *cannabis* it can be used in prescriptive *cannabis*.

An idealized dispensary will stock dried *cannabis*, chosen from cultivars to maximize their single cannabinoid, namely THCA, CBDA, CBCA, CBGA, THCVA, CBDVA, CBCVA, and CBGVA. These can be decarboxylated to provide their neutral partner. They can then be blended to achieve a ratio or precision decarboxylation can be used to produce a desired ratio in a given acidic/neutral cannabinoid pair.

The invention claimed is:

1. A process to make partial or complete decarboxylated *cannabis* comprising:
   providing a thin layer of pulverized *cannabis*, and
   heating the thin layer of pulverized *cannabis* by direct contact with a heat source for a specified time and temperature.

2. The process of claim 1, wherein the thin layer of pulverized *cannabis* is placed between two heating plates and heated by direct contact with the heating plates.

3. The process of claim 1, wherein the thin layer of pulverized *cannabis* is placed between two metallic foil layers and heated by direct contact with the metallic foil layers.

4. The process of claim 1, wherein the thin layer of pulverized *cannabis* is placed between two parchment layers which are further placed between metallic foil layers and/or heating plates.

5. The process of claim 1, wherein the thin layer of pulverized *cannabis* is placed between two parchment layers which are further placed in a mylar bag.

6. The process of claim 1, wherein the thin layer of pulverized *cannabis* is heated at 300-400° F.

7. The process of claim 1, wherein the thin layer of pulverized *cannabis* is heated at 300-350° F.

8. The process of claim 1, wherein the thin layer of pulverized *cannabis* is heated at 350-400° F.

9. The process of claim 1, wherein the thin layer of pulverized *cannabis* is heated for 15 seconds or less.

10. The process of claim 1, wherein the thin layer of pulverized *cannabis* is heated for 10-15 seconds.

11. The process of claim 1, wherein the thin layer of pulverized *cannabis* has a thickness of ⅛ inch of less.

12. The process of claim 1, wherein the thin layer of pulverized *cannabis* has a thickness of ¼ inch of less.

13. The process of claim 1, further comprising blending the decarboxylated *cannabis* with dried *cannabis* to obtain a target ratio of acidic to neutral cannabinoid.

* * * * *

UNITED STATES PATENT AND TRADEMARK OFFICE
CERTIFICATE OF CORRECTION

| | | |
|---|---|---|
| PATENT NO. | : 11,254,633 B2 | |
| APPLICATION NO. | : 16/602455 | |
| DATED | : February 22, 2022 | |
| INVENTOR(S) | : Jonas Alcirdas Navickas | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 144 days.

Signed and Sealed this
First Day of November, 2022

Katherine Kelly Vidal
*Director of the United States Patent and Trademark Office*